(12) United States Patent
Cutler et al.

(10) Patent No.: US 7,469,158 B2
(45) Date of Patent: Dec. 23, 2008

(54) FETAL OXIMETRY SYSTEM AND SENSOR

(75) Inventors: Christopher A. Cutler, Centerville, UT (US); William D. Wallace, Salt Lake City, UT (US); Steven R. Smith, Draper, UT (US); Daniel J. McGraw, Herriman, UT (US); Nick Tu, West Palm Beach, FL (US); Clifford G. Montagnoli, Murray, UT (US); Trent W. Banks, Salt Lake City, UT (US)

(73) Assignee: RIC Investments, LLC, Murrysville, PA (US)

( * ) Notice: Subject to any disclaimer, the term of this patent is extended or adjusted under 35 U.S.C. 154(b) by 766 days.

(21) Appl. No.: 10/957,430

(22) Filed: Oct. 1, 2004
(Under 37 CFR 1.47)

(65) Prior Publication Data
US 2005/0283059 A1    Dec. 22, 2005

Related U.S. Application Data

(62) Division of application No. 09/581,122, filed as application No. PCT/US98/12394 on Jun. 15, 1998, now abandoned.

(60) Provisional application No. 60/050,958, filed on Jun. 17, 1997.

(51) Int. Cl.
*A61B 5/1455* (2006.01)

(52) U.S. Cl. .................. 600/338; 600/325; 600/339

(58) Field of Classification Search ................. 600/313, 600/325, 328, 338, 339, 351
See application file for complete search history.

(56) References Cited

U.S. PATENT DOCUMENTS

| | | | |
|---|---|---|---|
| 3,638,640 A | | 2/1972 | Shaw |
| 3,847,483 A | | 11/1974 | Sidlauskas et al. |
| 4,281,659 A | * | 8/1981 | Farrar et al. .................. 600/351 |
| 4,320,764 A | * | 3/1982 | Hon ........................... 600/351 |
| 4,658,825 A | | 4/1987 | Hochberg et al. |
| 4,714,341 A | | 12/1987 | Hamaguri et al. |
| 4,830,013 A | | 5/1989 | Maxwell |
| 4,840,179 A | | 6/1989 | Ullrich |
| 4,882,492 A | | 11/1989 | Schlager |
| 4,913,151 A | * | 4/1990 | Harui et al. .................. 600/313 |
| 5,058,588 A | | 10/1991 | Kaestle |
| 5,218,912 A | | 6/1993 | Mannheimer et al. |
| 5,361,757 A | | 11/1994 | Smith et al. |
| 5,377,677 A | * | 1/1995 | Dowd et al. .................. 600/376 |
| 5,388,579 A | | 2/1995 | Dowd et al. |
| 5,411,024 A | * | 5/1995 | Thomas et al. ............... 600/325 |
| 5,417,207 A | | 5/1995 | Young et al. |
| 5,419,322 A | * | 5/1995 | Joseph et al. ................ 600/338 |
| 5,497,769 A | | 3/1996 | Gratton et al. |
| 5,524,617 A | | 6/1996 | Mannheimer |
| 5,529,064 A | | 6/1996 | Rall et al. |
| 5,551,424 A | | 9/1996 | Morrison et al. |
| 5,662,103 A | | 9/1997 | Smith et al. |
| 5,743,260 A | | 4/1998 | Chung et al. |
| 5,782,237 A | | 7/1998 | Casciani et al. |
| 5,782,756 A | | 7/1998 | Mannheimer |
| 6,226,540 B1 | | 5/2001 | Bernreuter |
| 6,298,253 B1 | | 10/2001 | Buschmann |

FOREIGN PATENT DOCUMENTS

| | | |
|---|---|---|
| EP | 0135840 | 4/1985 |
| EP | 0631137 | 12/1994 |
| WO | WO 89/09016 | 10/1987 |
| WO | WO9611623 | 4/1996 |

OTHER PUBLICATIONS

Niiland et al., "Reflectance Pulse Oximetry (RPOX): Two Sensors Compared in Piglets", Abstract only (date unknown).

Knitza et al., "Influence of Caput Succedaneum and Hair on Fetal O2-Saturation Measured by Pulse Oximetry", Abstract only, (date unknown).

Dildy et al., "Intrapartum Fetal Pulse Oximetry: The Effects of Variable Decelerations on Fetal Ariterial Oxygen Saturation", Abstract only, (date unknown).

Van Hook et al., "Increases in Human Fetal Hemoglobin Oxygen Saturation During Late Fetal Heart Rate Decelerations as a Response to Intrauterine Stress", Abstract only, (date unknown).

Anderson et al., "The Effects of Maternally-Administered Oxygen on Human Fetal SPO2 Values During Labor", Abstract only, (date unknown).

Schaffer et al., "Fetal Pulse Oximetry: Correlation of O2-Saturation During Labor and the Fetal Outcome", Abstract only, (date unknown).

Barker et al., "Pulse Oximetry: Applications and Limitations", Article, (date unknown).

Luttkus et al., "Continuous Monitoring of Fetal Oxygen Saturation by Pulse Oximetry", Article, Obstetrics & Gynecology, vol. 85, No. 2, Feb. 1995.

Johnson et al., "Fetal Pulse Oximetry: A New Method of Monitoring the Fetus", Article, Aust NZ J Obstet Gynaecol, 1994.

Pologe, "Pulse Oximetry: Technical Aspects of Machine Design", Article, (date unknown).

\* cited by examiner

*Primary Examiner*—Eric F Winakur
*Assistant Examiner*—Etsub D Berhanu
(74) *Attorney, Agent, or Firm*—Reed Smith LLP

(57) ABSTRACT

An optical measuring device having multiple optical paths between one or more light emitters and one or more light detectors and/or providing at least two sets of wavelength of light along at least one path, with a final measurement being produced as a combination of measurements of the sets of wavelengths of light taken along one or more of the optical paths. Features that contribute to increased safety and ease of use include providing (1) a receiving cavity in a proximal end of an insertion rod that holds a free end of a circuit connector to keep it from becoming tangled or snagged, (2) a mechanism to keep the sensor within an introducer tube during storage and insertion and to expose a portion of the sensor only when the sensor is applied to the unborn baby, (3) a tab on the insertion rod to prevent the circuit connector from becoming tangled or snagged within the introducer tube, (4) a rotating feature whereby if a torque applied on the sensor exceeds a first predetermined amount, the sensor rotates, and a disengaging feature whereby the sensor detaches from insertion rod if a pull-off force exceeds a second predetermined amount, the rotating and disengaging features being independent of one another, (5) a circuit connector that includes at least one of the following features: (a) a stiffening member provided at the proximal end to minimize bending, (b) a shielding layer, and (c) at least one slit to increase the flexibility of the circuit connector, and (6) an interface that includes an identification element that is detected by an external circuit only if the circuit connector is connected to the interface. The present invention also pertains to a method of manufacturing a needle that is used in an invasive sensor, and preferably for fetal monitoring, that provides features not heretofore available in conventional sensors.

3 Claims, 16 Drawing Sheets

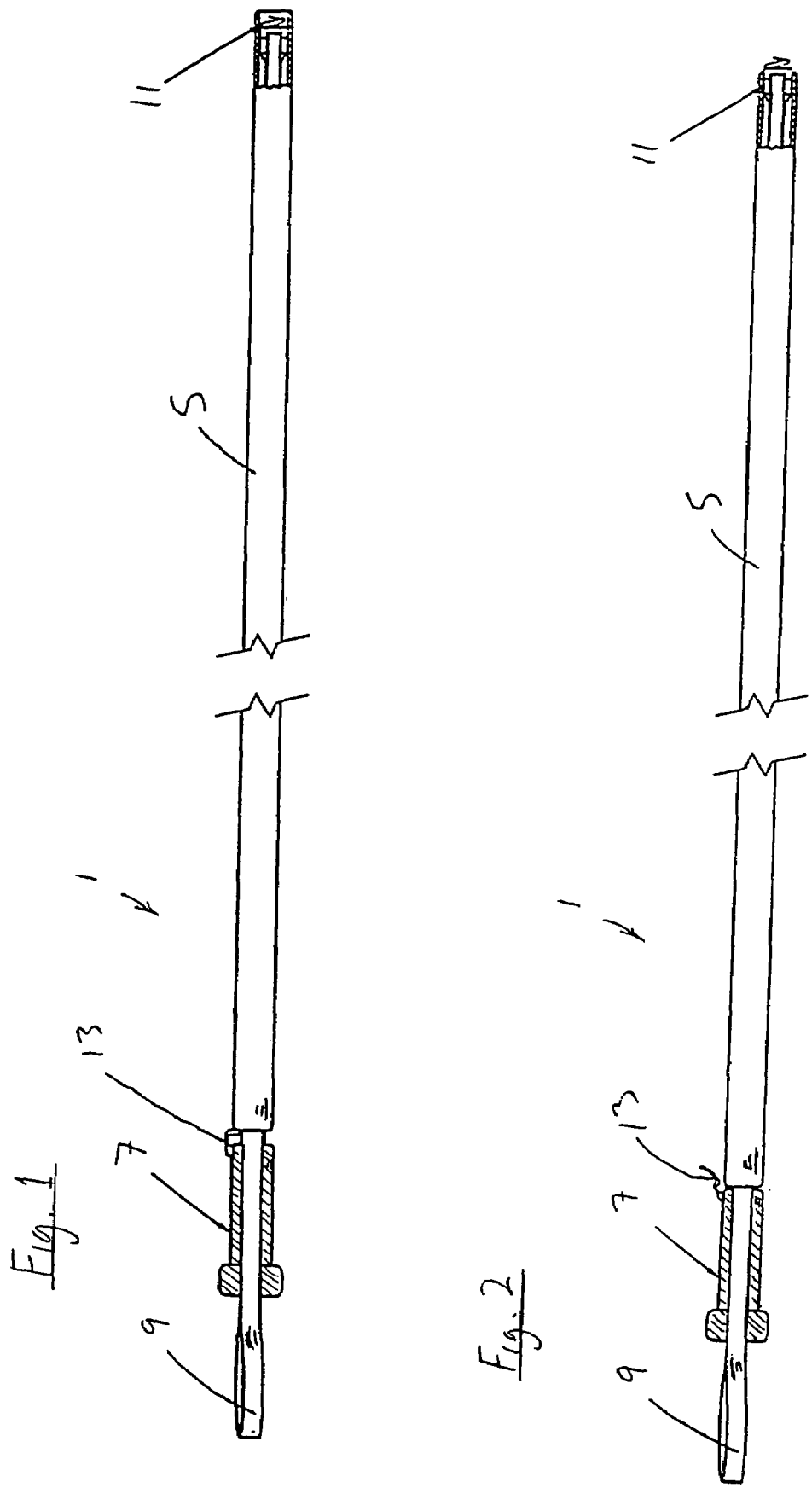

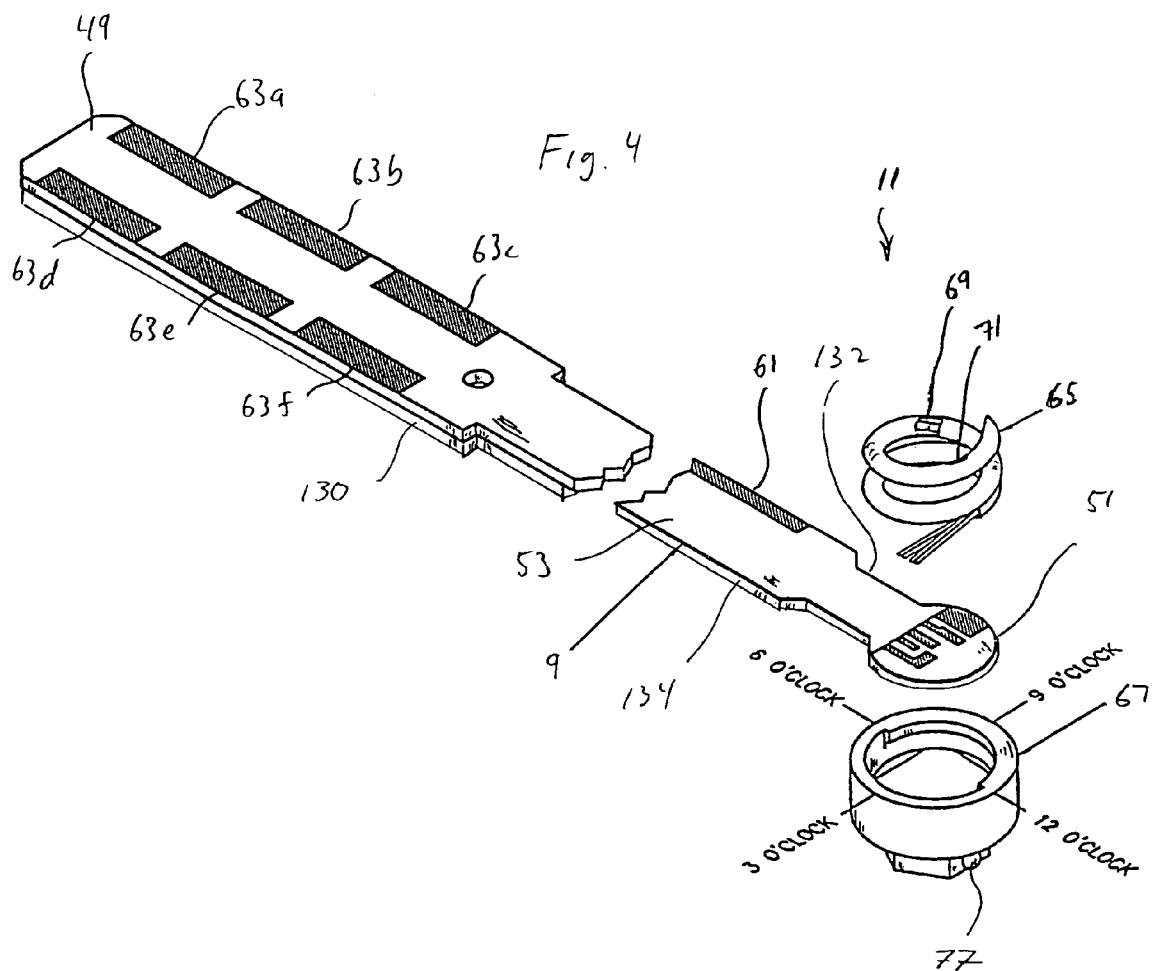

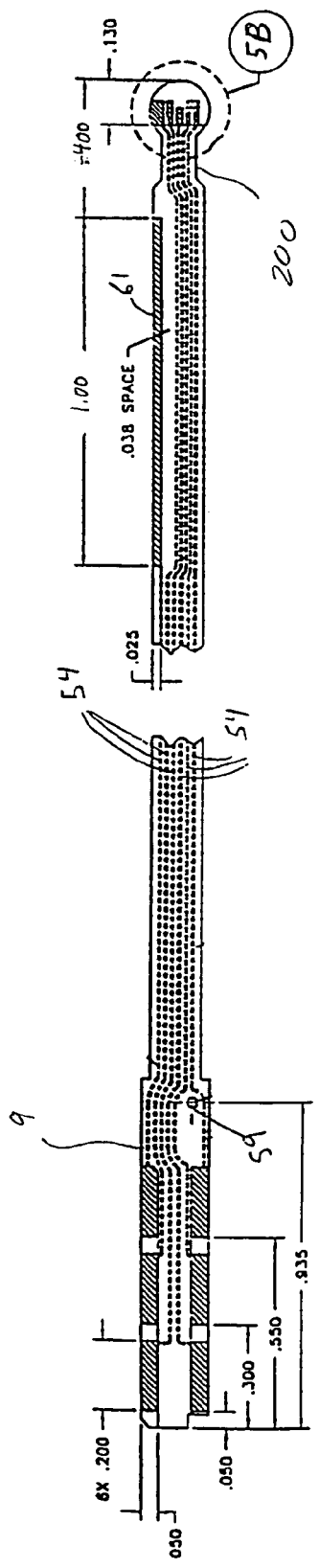
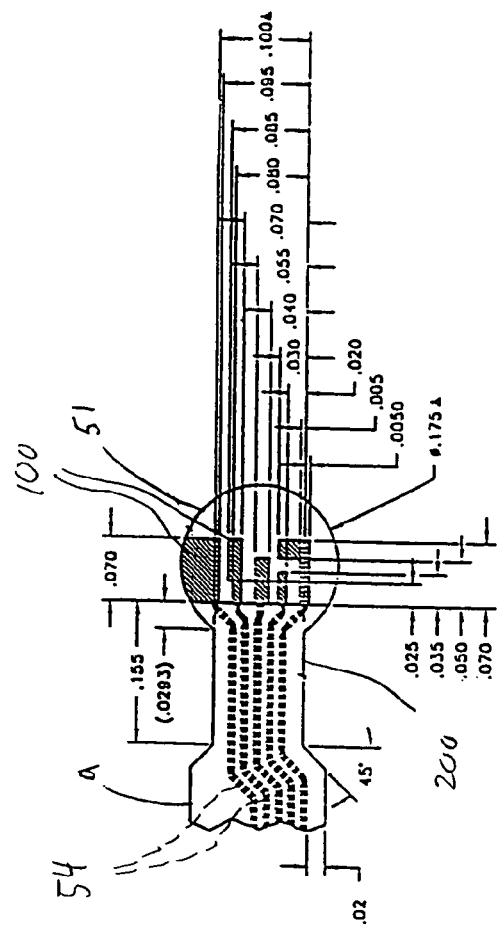
Fig. 5A
Fig. 5B

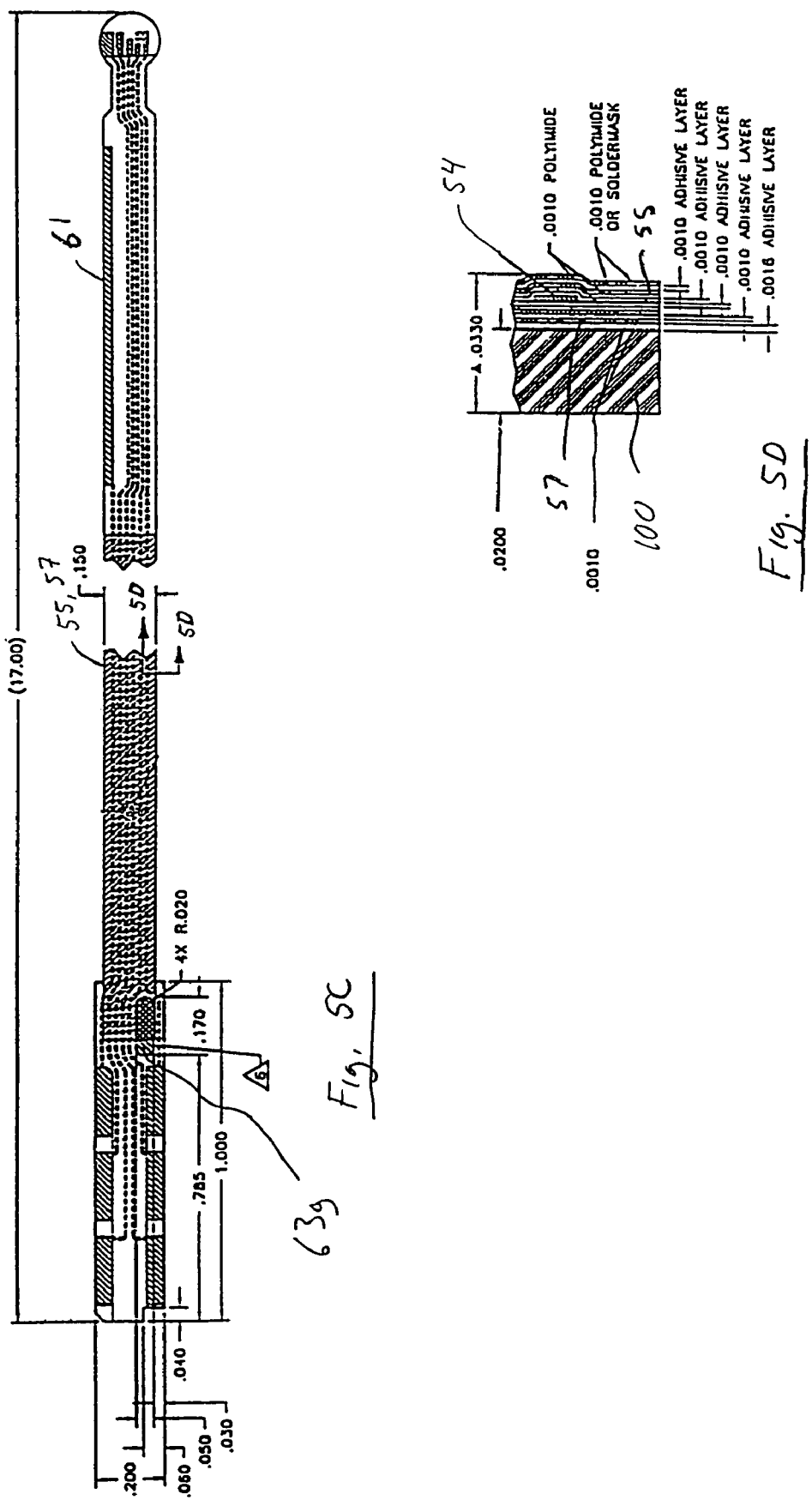

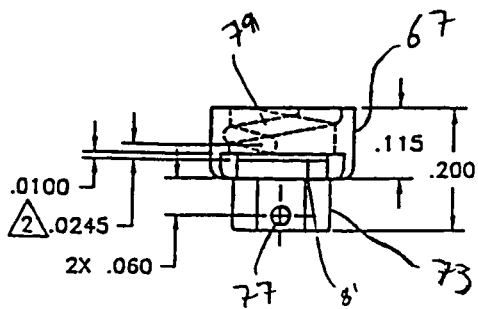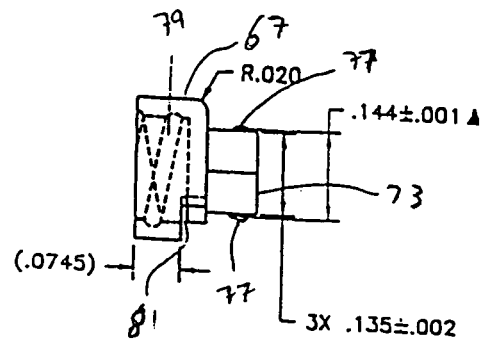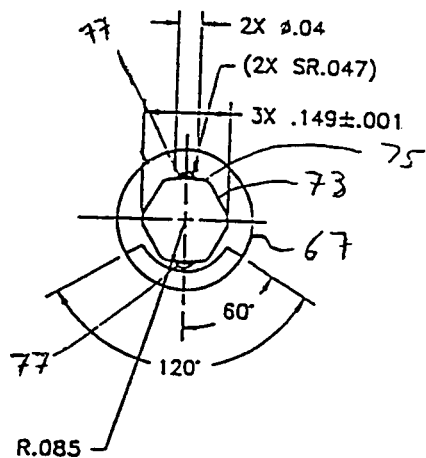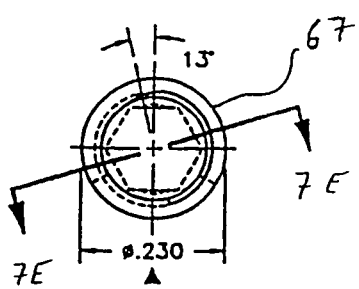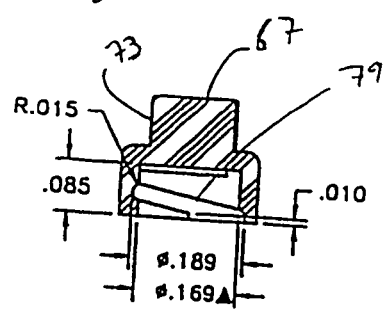

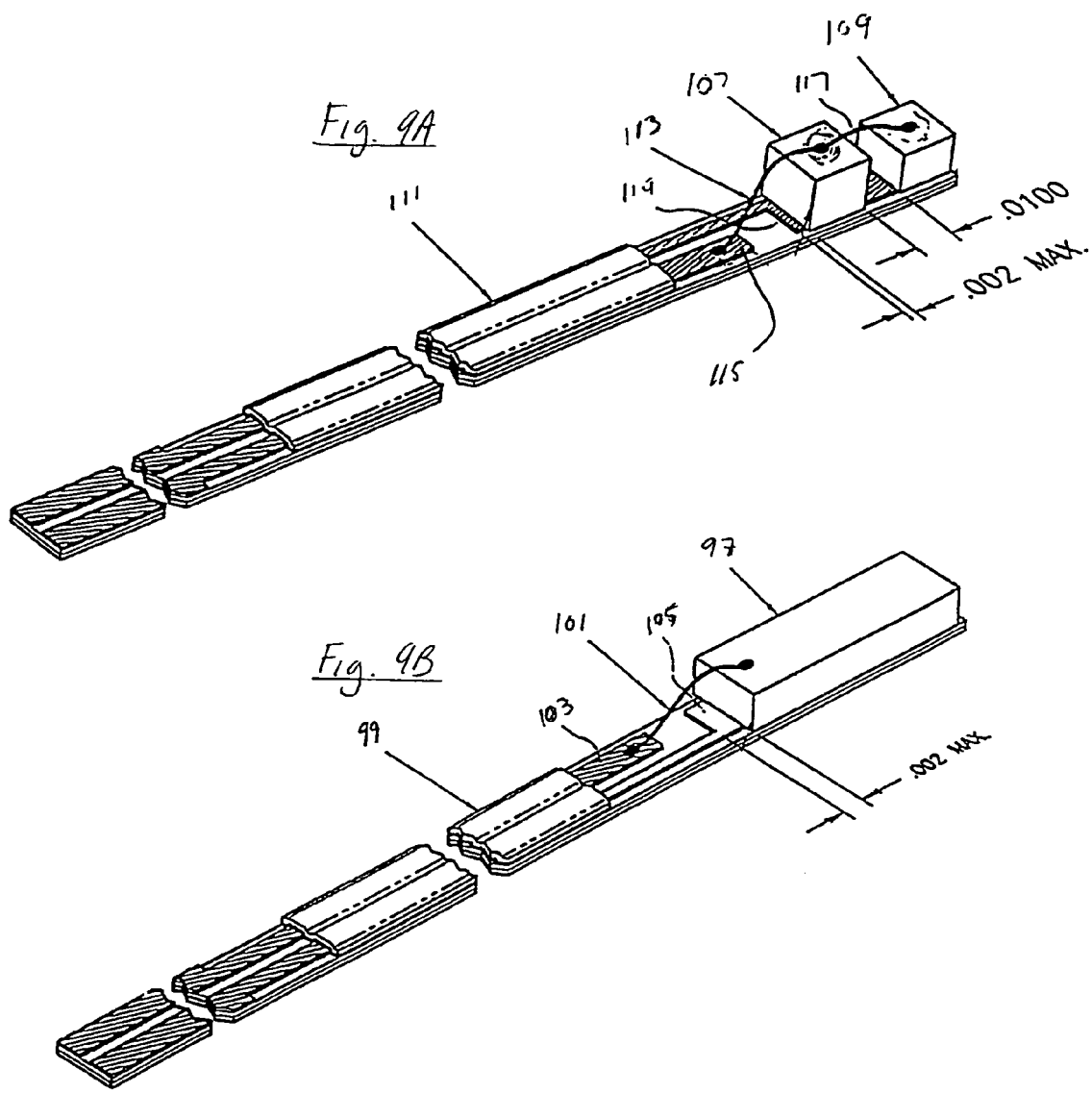

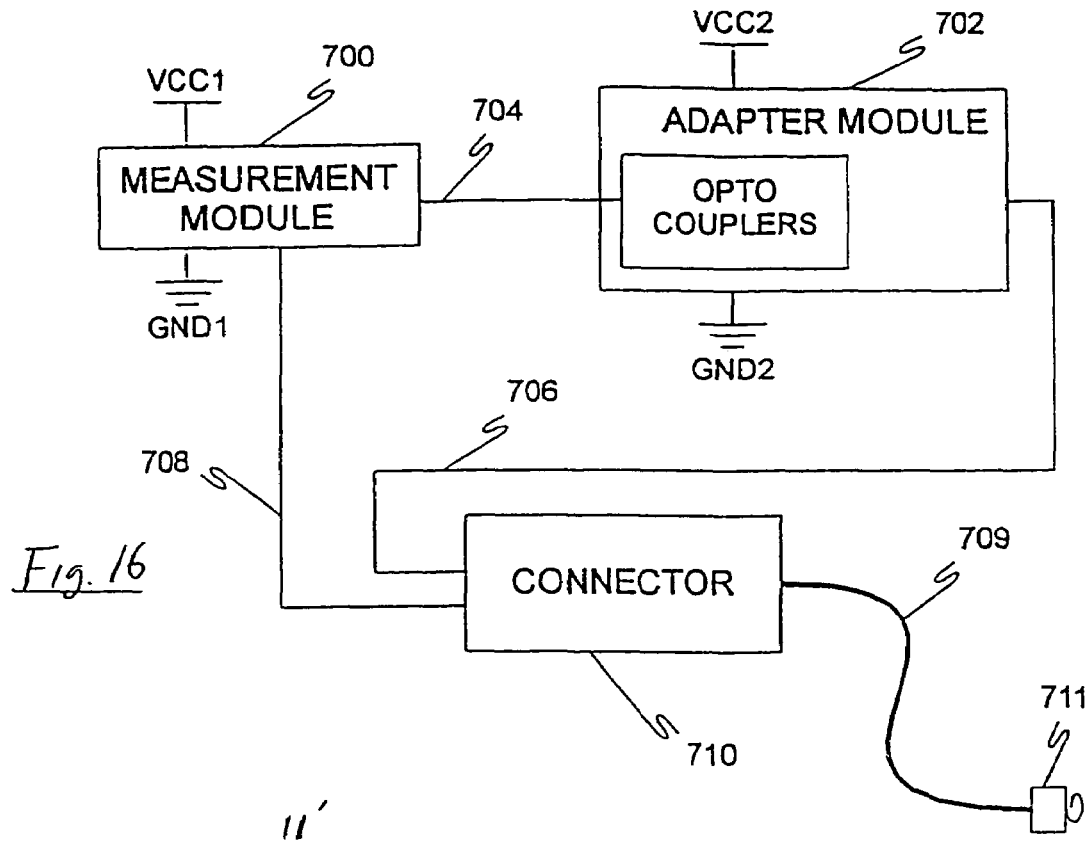
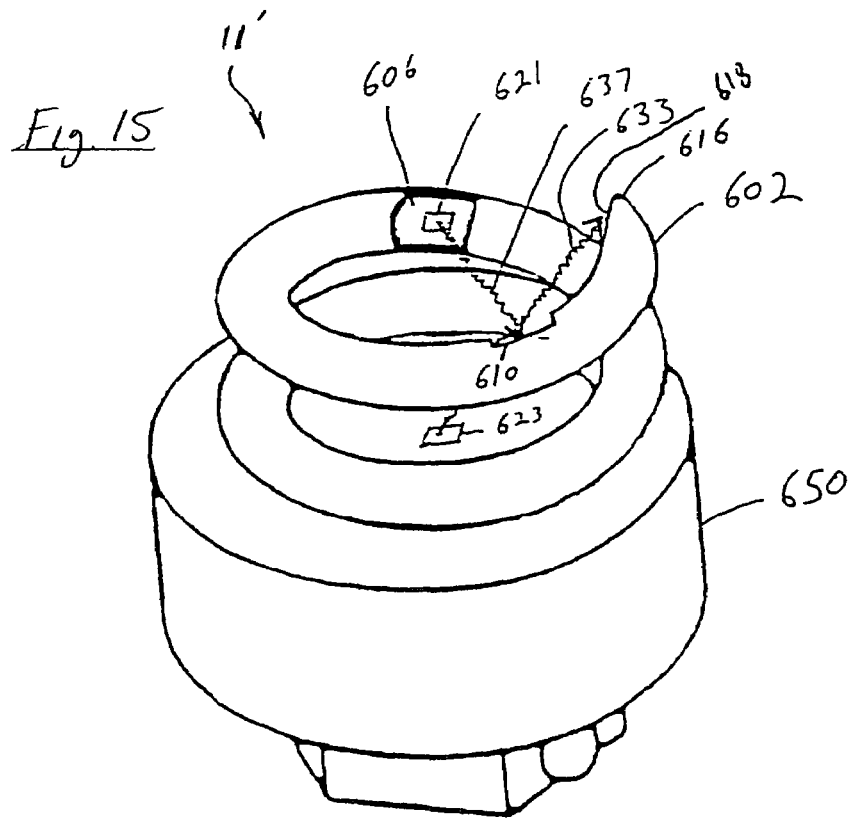

FETAL OXIMETRY SYSTEM AND SENSOR

This application is a divisional application pursuant to 35 U.S.C. §120 of earlier filed U.S. patent application Ser. No. 09/581,122 filed Jan. 14, 2002, now abandoned, which was a national phase application pursuant to the Patent Cooperation Treaty, of International Application Serial No. PCT/US98/12394, filed Jun. 15, 1998, which claimed priority to Provisional Application Ser. No. 60/050,958, filed Jun. 17, 1997.

TECHNICAL FIELD

The present invention relates generally to optical measurement devices, and more particularly to fetal oximetry systems and sensors with improved accuracy, reliability, safety and ease of use. The invention further relates to a method of making and using such devices.

BACKGROUND ART

Oximetry is based on the principle that the color of blood is related to the oxygen saturation level ($SaO_2$) in the blood. For example, as blood deoxygenates, skin loses its pinkish appearance and takes on more of a bluish tint. Current pulse oximeters operate by applying at least one wavelength of light to the patient and measuring the intensity of the light passing therethrough. The pulse oximetry oxygen saturation level ($SpO_2$) is derived from a ratio of relative light intensities. Light absorption through tissue is generally constant for a particular subject, with the exception of the arterial blood, which causes the light absorption to vary with the flow of blood. Thus, the absorption of light through tissue has a pulsatile (AC) component and a constant (DC) component. Because the pulsing is only a function of the fluctuating volume of arterial blood, the AC light intensity level represents the absorption of only the $O_2Hb$ and $RHb$ molecules. By measuring only the pulsatile light, pulse oximetry effectively ignores the absorbencies of other tissue material positioned between light source and light detector.

To identify the oxygen saturation level, two wavelengths of light are typically used with different absorption curves such that the ratio of the two absorptions is unique from 0% saturation through 100% saturation. $SpO_2$ can be derived by positioning the tissue between a light source and a detector, passing a light of each of two wavelengths through the tissue, measuring the pulsatile light intensity from each wavelength, determining the ratio of the light intensities, and correlating the ratio to a unique position along a combined absorption curve for the two wavelengths.

To determine a ratio of pulsatile light intensities, the constant component of the light intensity must be factored out. The amplitudes of both the AC and DC components are dependent on the incident light intensity. Dividing the AC level by the DC level gives a corrected AC level that is no longer a function of the incident light intensity. Thus, the ratio $R=(AC1/DC1)/(AC2/DC2)$ is an indicator of arterial $SaO_2$. Conventionally, an empirically derived calibration curve for the relationship between the above ratio and $SaO_2$ provides the pulse oximetry oxygen saturation level $SpO_2$.

Pulse oximeters have gained rapid acceptance in a number of medical applications. Because the light source and detector can be applied to the outside of tissue area, such as to an ear lobe or finger tip, pulse oximeters are a highly non-invasive source of diagnostic information. Pulse oximeters are utilized, for example, in the operating room by anesthesiologists to monitor oxygen saturation levels. Pulse oximeters are also used in doctors' offices to monitor and diagnose respiratory problems such as sleep apnea. More recently the usefulness of pulse oximeters in fetal monitoring has gained considerable attention.

During labor and delivery, it is desirable to know the oxygen saturation level in the baby as a predictor of when emergency procedures, such as cesarean section, might be necessary. However, current pulse oximeters have generally failed to obtain clinical acceptance as a primary indicator of fetal oxygen saturation level. One possible reason is that the non-invasive nature of most pulse oximeters leaves them susceptible to motion artifact problems on the part of the mother and the unborn baby. For example, in a conventional pulse oximeter, a single probe, i.e., containing both the light source and detector is typically positioned against the baby's scalp or cheek and held in place by the pressure of the mother's uterus on the probe. During contractions, the probe could be dislodged or the variation in pressure of the contraction itself might alter the optical path and upset the reading. Obviously, such a probe would become dislodged during the final stages of delivery. A result is that the usable signal time from a conventional pulse oximeter can range anywhere from 20 to 80 percent of the total time the pulse oximeter is monitoring the subject.

Other concerns with pulse oximeters for monitoring fetal oxygen saturation level are poor signal quality because of poor probe contacts, merconium staining (fetal bowel movement), vernix (a cheesy fetal skin covering), hair, and caput formation (swelling in the scalp). Furthermore, certain assumptions are made regarding the consistency of light absorption through tissue. For example, among other things, a variation typically occurs between $SpO_2$ and $SaO_2$, thereby degrading the accuracy of the oximeter.

In addition, the use of pulse oximeters to monitor fetal oxygen saturation level presents other difficulties. For example, the caregiver placing the oximetry sensor on the unborn baby must do so while the baby remains in the mother's womb, thereby limiting the caregiver's view and maneuverability in placing the sensor on the baby. Also, the sensor must remain in place during labor. Furthermore, the sensor provided on the unborn baby can only be used once. Therefore, the cost of the sensor should be kept at a minimum.

Many of the above problems related to the optical measurement of oxygen saturation are also present in other optical measurement applications, such as optical measurement of blood glucose, bilirubin, and hemoglobin.

DISCLOSURE OF THE INVENTION

Accordingly, it is an object of the present invention to provide an apparatus that overcomes the shortcomings of conventional optical measurement devices and techniques. In particular, the present invention provides an optical measurement device with improved accuracy and usable signal time. According to one aspect of the invention, this object is achieved by providing an optical measuring device that utilizes multiple optical measurement paths. For example, an optical measuring device according to one embodiment of the present invention includes a sensor having a light emitter for generating light along two or more optical measurement paths through a tissue and a light detector for detecting light along each of the optical measurement paths. A processing system controls the light generated by the light emitters, measures the light incident upon the light detectors, and produces a measurement, which, in one embodiment of the invention, is a measurement common to each optical measurement path but distributed independently in each optical path, such as oxygen saturation level in blood.

As used herein, a common measurement is distributed independently if it is affected by optical path dependent factors, such as sensor contact, tissue composition, and other path specific variables. In another embodiment, the measurement includes a different measurement associated with each optical measurement path, e.g., peculiar to a particular optical path.

According to another aspect of the invention, the above object is achieved by causing the measuring device to produce at least two distinct sets of wavelengths of light, each set containing at least two distinct wavelengths of light. The processing unit produces a measurement according to selectively weighted ratios of the light measured from the sets of wavelengths along any one of the optical measurement paths or along any combination of optical measurement paths including all optical measurement paths. In a preferred embodiment, the light emitter generates at least four wavelengths of light, and the processing system produces a measurement according to selectively weighted ratios of the light measured from a pair of or a combination of pairs of any two of the wavelengths.

In a further embodiment of the invention, the sensor includes light emitters and light detectors disposed along multiple optical paths and are located on a single probe. This probe includes a spiral hollow needle suitable for screwing into the tissue. In an exemplary embodiment, the needle includes a number of window areas suitable for light emission and light detection and light is carried through the needle by light transmitting fibers. The light transmitting fibers can be housed in the spiral hollow needle in proximity to the window areas to either generate or detect light.

In yet another embodiment according to the invention, at least one additional sensor device for measuring further parameters is coupled to the measuring unit to correlate all of the measurements, such as, charting EKG measurements together with $SpO_2$ measurements.

Another embodiment of the invention provides a measuring device that includes a sensor having light emitters for generating light at least three distinct wavelengths and light detectors for detecting light at each of the wavelengths.

Another object of the present invention is to provide a physiological condition measuring device that is particularly suited for use in measuring a physiological condition of the unborn baby. This object is achieved according to one embodiment of the present invention by providing a physiological condition measuring device that includes an insertion rod, a sensor that selectively attaches to the distal end of the insertion rod, a circuit connect that connects the sensor to an external circuit, and an introducer tube that houses at least a portion of the insertion rod, sensor and circuit connector. In this embodiment, the insertion includes a receiving cavity in its proximal end opposite from the sensor to house a free end of the circuit connector to keep the free end from becoming tangled or snagged during application.

In another embodiment, the measuring device includes a mechanism that selectively couples the insertion rod and the introducer tube to maintain these items in a first position relative to one another with the sensor being located entirely within the introducer tube. This mechanism also permits the introducer tube to be moved to a second position relative to the insertion rod wherein at least a portion of the sensor is located outside said introducer tube. Thus, the sensor can be kept within the introducer tube during storage and insertion into the mother and exposed only upon applying the sensor to the unborn baby, thereby preventing the exposed sensor from being contaminated, damaged or from harming others, such as the mother.

Yet another embodiment of the present invention provides a tab on the insertion rod extending between the insertion rod and the introducer tube. The tab is sized and configured so as to contact a portion of the circuit connector during rotation of the insertion rod relative to the introducer tube to urge the circuit connector to rotate in a same direction of rotation as said insertion rod. This feature of the present invention prevents the circuit connector from becoming tangled or snagged within the introducer tube.

In another embodiment of the present invention, the sensor and insertion rod are sized and configured such that the sensor rotates relative to the insertion rod if a torque applied on the sensor by the insertion rod exceeds a first predetermined amount. Also, the sensor and insertion rod are sized and configured such that the sensor disconnects from the insertion rod if a pull-off force exerted on the sensor by the insertion rod exceeds a second predetermined amount. The mechanism that facilitates rotation and the mechanism that facilitates detachment of the sensor are independent of one another so that the first predetermined amount of torque necessary to cause rotation is independent of the second predetermined amount of force necessary to cause said sensor to disconnect from said insertion rod, thereby making the measuring device more flexible in its design and application than conventional devices.

In still another embodiment of the present invention, the circuit connector includes at least one of the following features: (a) a stiffening member provided at the proximal end to minimize bending, (b) a shielding layer disposed on at least one side of a conductor located in the circuit connector, and (c) at least one slit extending at least partially into the circuit connector in a longitudinal direction thereof to increase the flexibility of the circuit connector.

Another embodiment of the present invention provides an interface that selectively couples to the proximal end of the circuit connector. The interface includes an identification element. The circuit connector is configured such that connecting the circuit connector to the interface operatively couples the identification element to an external circuit that enables the external circuit to detect the identification element.

It is still another object of the present invention to provide a method a manufacturing a needle that is used in an invasive sensor, and preferably for fetal monitoring, that provides features not heretofore available in conventional sensors. According to one embodiment of the present invention, this object is achieved by providing a method of forming a needle for use in a physiological condition measuring devices that includes the steps of: bending a hollow tube into a "J" shape, beveling a first end of the tube proximate to the bend in at least three planes to define a point, further bending the tube from the "J" shape to a "P" shape, defining at least one opening in the tube at a location generally facing a center of a circular portion of the "P" shape, threading an optical element into a second end of the hollow tube until a portion of the optical element is located in the window, securing the optical element in place within the tube, and further bending the tube into a spiral configuration.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 1 is a fragmented side view of the sensor system, showing an introducer tube, insertion rod, circuit connector, and sensor according to the principles of the present invention, with the sensor inside the introducer tube;

FIG. 2 is a fragmented side view of the sensor system shown in FIG. 1 with the sensor protruding from the introducer tube;

FIG. 4 is an exploded, perspective view illustrating a circuit connector, hollow spiral needle and cup;

FIGS. 5A-5C are detailed views of an exemplary embodiment of the circuit connector and FIG. 5D is a sectional view taken alone line 5D-5D in FIG. 5C;

FIGS. 7A-7D show views of the cup portion of the sensor, and FIG. 7E is a sectional view taken along section line 7E-7E in FIG. 7D;

FIGS. 9A and 9B are fragmented, perspective views of the LED circuit and photodetector circuit, respectively, according to the principles of the present invention;

FIG. 15 is a perspective view of a probe that utilizes the spiral needle illustrated in FIG. 14;

FIG. 16 is a schematic diagram of a sensor system of another embodiment of the present invention.

BEST MODE FOR CARRYING OUT THE INVENTION

Figure 3A:
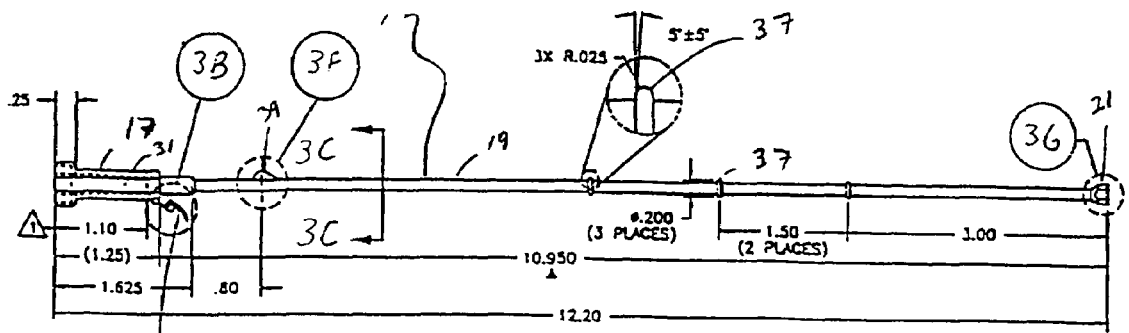
FIG. 3A is a detailed view of a preferred embodiment of the insertion rod according to the principles of the present invention.

The following is a detailed description of an example of components and assembly procedures for manufacturing a preferred embodiment of a fetal pulse oximetry sensor system according to the invention. Numerous aspects of the invention are set forth with respect to specific parts of the sensor system and their assembly procedures. This description should be considered as illustrative and not limiting. FIGS. 2 and 3 are elevational views showing a sensor system 1 according to the principles of the present invention. Sensor system 1 includes an introducer tube 5, an insertion rod 7, a circuit connector 9, and a sensor 11. Each of these components of sensor system 1 are hereinafter described in detail, along with related assembly procedures.

I. Introducer Tube

Introducer tube 5 is a length of hollow tubing cut to a precut length, for example, 11.05 inches. Preferably, the tubing is made of a biologically compatible plastic, such as polypropylene or polycarbonate, and has rounded edges. Preferably, the inner diameter of introducer tube 5 is 0.246 inches and the outer diameter is 0.310 inches. Both ends of introducer tube 5 are preferably rounded with a radius of 0.035 inches. Although the embodiment shown in FIGS. 1 and 2 illustrates a straight introducer tube 5, other shapes may be used. For example, in an alternative embodiment of the sensor system, the introducer tube is bent at an angle of between 0°-90°.

II. Insertion Rod

FIG. 3A is a detailed, dimensioned illustration of a preferred embodiment of insertion rod 7 according to the principles of the present invention. Generally, insertion rod 7 includes a handle 17, a shaft 19, and an applicator 21, each of which is hereinafter described in detail. Insertion rod 7 is preferably integrally formed and made of a biologically compatible plastic material, such as AMOCO 7234 with omnicolor 2%. However, the various parts of insertion rod 7 may be separately formed and made of other materials, such as metal or wood.

A. Handle

Handle 17 is used for pushing insertion rod 7 into introducer tube 5 and for pushing the insertion rod against the presenting portion of the unborn baby (usually the baby's head) and for turning insertion rod 7 to attach sensor 11 to the baby. According to the invention, handle 17 has several advantageous features.

1. Tab

Figure 3B:
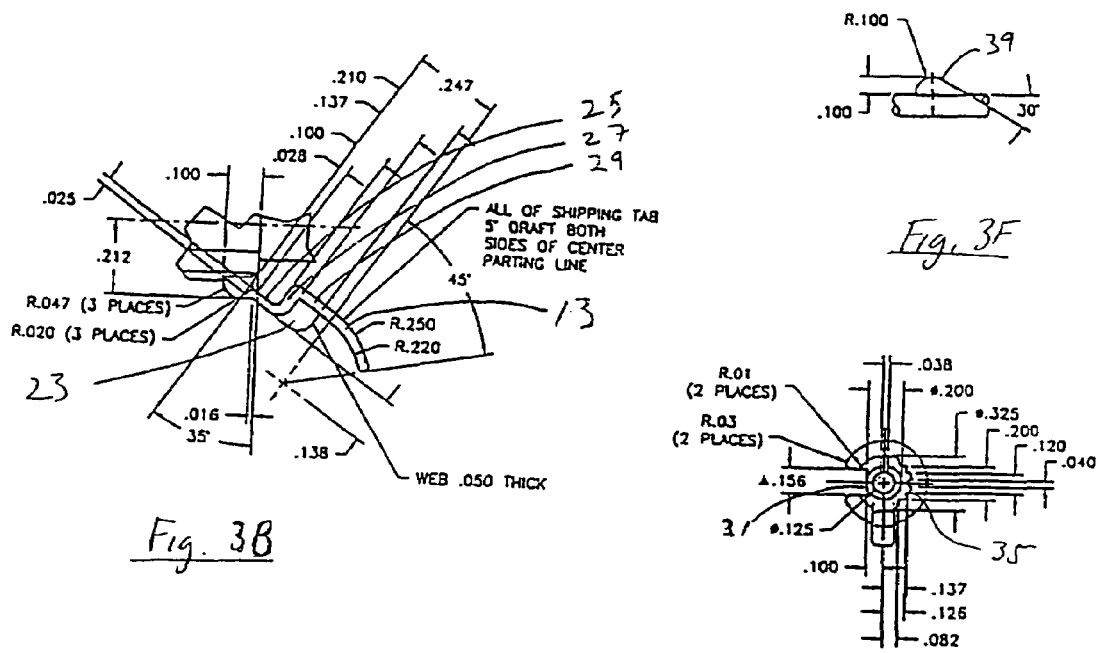
FIG. 3B is an enlarged view of a portion of the rod illustrated in FIG. 3A.
Figure 3F:
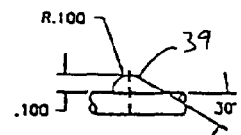
FIG. 3F is an enlarged view of FIG. 3A showing details of a ramp-shaped tab.

Referring to FIGS. 1, 2 and 3B, a tab 13 is provided on insertion rod 7 to prevent sensor 11 from protruding out of the end of introducer tube 5 when an end of tab 13 is inserted within the distal end of introducer tube 5 as shown in FIG. 1. This feature provides an advantage of protecting sensor 11 during shipping and when not in use by keeping sensor 11 inside relatively rigid introducer tube 5. Also, keeping sensor 11 inside introducer tube 5 minimizes the likelihood that sensor 11 will cut or tear its sterile storage pouch. A further advantage of greater safety and comfort provided by keeping sensor 11 inside introducer tube 5 occurs when introducing sensor 11 into the patient's vagina. Maintaining sensor 11 inside introducer tube 11 minimizes the likelihood the patient will be punctured or cut by the sensor. When tab 13 is not inserted within the proximal end of introducer tube 5, sensor 11 protrudes from the end of introducer tube 5. See FIG. 2.

According to the invention, insertion rod 7 remains inside introducer tube 5 when inserting the introducer tube into the patient's vagina. After introducer tube 5 is fully inserted, insertion rod 7 is slightly withdrawn from introducer tube 5 to allow tab 13 to disengage, i.e. to become untucked from introducer tube 5 as shown in FIG. 2. Thereafter, either insertion rod 7 is moved back into introducer tube 5 or introducer tube 5 is slightly withdrawn while holding insertion rod 7 in place, to allow sensor 11 to protrude from the end of the introducer tube. Sensor 11 is then in position to be attached to the baby.

According to the present invention, tab 13 is sufficiently resilient such that when the end of tab 13 exits introducer tube 5, the end of tab 13 springs outwardly away from insertion rod 7 to clear the lip of introducer tube 5. Thus, when insertion rod 7 is moved back into introducer tube 5, tab 13 does not obstruct the movement. This feature provides the advantage that disengaging the tab may be performed "hands-free" without having to manually move tab 13 out of the way.

As shown in greater detail in FIG. 3B, which is an enlarged view of tab 13, tab 13 is provided on the handle 17 near an end thereof proximate to shaft 19. Tab 13 includes a first leg 25, a second leg 27, and a third leg 29. Second leg 27 is formed approximately at a 90° angle relative to first leg 25, and third leg 29 is formed approximately at a 90° angle relative to second leg 27 and is bent outwardly at its distal end.

The inner diameter of introducer tube 5 accommodates both shaft 19 and third leg 29. When third leg 29 is tucked inside introducer tube 5, the length of second leg 27 extends sufficiently beyond the inner diameter of introducer tube 5 so that second leg 27 blocks further insertion of insertion rod 7 into introducer tube 5. First leg 25 has a length that sufficiently prevents the sensor from protruding out of the end of introducer tube 5, in accordance with the length of insertion rod 7 and introducer tube 5. For example, if introducer tube 5 has a length that is slightly shorter than the overall length of shaft 19 and applicator 21 with sensor 11 installed, i.e., such that the needle portion of sensor 11 protrudes out of the end of introducer tube 5, then the length of first leg 25 should be at least slightly longer than the distance that the needle portion of sensor 11 protrudes out of the end of introducer tube 5.

As shown in FIG. 3B, tab 13 includes a web 23, which does not fit into introducer tube 5 when the end of tab 13 is tucked inside introducer tube 5, i.e., acts as a stopper. Preferably, as shown in FIG. 3B, web 23 is about the same height as second leg 27. However, web 23 may be shorter or longer than second leg 27, as long as web 23 blocks insertion rod 7 from further insertion into introducer tube 5. The combined length of first leg 25 and web 23 should be made sufficient to prevent sensor 11 from protruding from the end of introducer tube 5 when third leg 29 is tucked inside introducer tube 5.

2. Slot

Figure 3C:
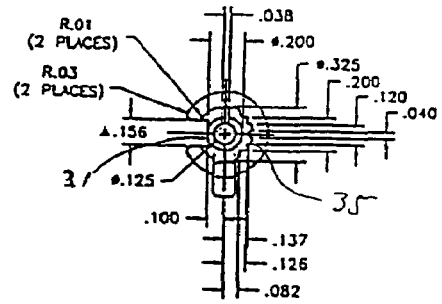
FIG. 3C is a sectional view taken along line 3C-3C in FIG. 3A.
Figure 3D:
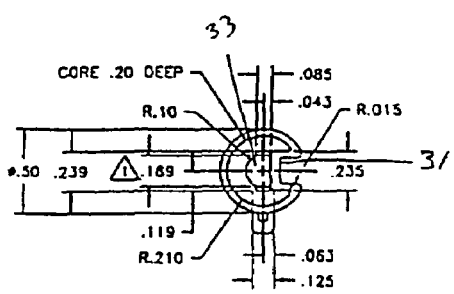
FIG. 3D is an end view of the insertion rod from the handle end of FIG. 3A.

As best shown in FIG. 3C, handle 17 includes a slot 31 that accommodates circuit connector 9. FIG. 3C is a sectional view taken along section line 3C-3C in FIG. 3A. FIG. 3D is an end view of insertion rod 7 when viewed from handle 17 end. As shown in FIGS. 3A, 3C, and 3D, slot 31 runs the entire length of handle 17. The width of slot 31 is at least slightly wider than the width of circuit connector 9 to receive the portion of circuit connector 9. When turning handle 17 to attach sensor 11 to the baby, circuit connector 9 is positioned in slot 31 and is kept in place, for example, by having the user place a thumb or a finger over the slot. In this manner, circuit connector 9 and insertion rod 7 rotate together to prevent circuit connector 9 from becoming twisted inside introducer tube 5.

3. Hollow End

As can be seen in FIG. 3D, handle 17 includes a hollow portion or cavity 33 extending generally in an axial direction along the longitudinal axis thereof. Cavity 33 is sized and configured to hold the interface end, i.e., the proximal end, of circuit connector 9. As shown in FIGS. 1-2, for shipping purposes, the interface end of circuit connector 9 is looped around and inserted in cavity 33. Preferably, the width of cavity 33 gradually tapers along its length so that gently pushing the interface end of circuit connector 9 into cavity 33 causes the interface end of circuit connector 9 to become wedged into cavity 33, thereby holding circuit connector 9 in place.

In the illustrated embodiment, cavity 33 is a generally rectangular opening with a flat face adjacent to slot 31 and a semicircular opening opposite to slot 31. However, other shapes are possible so long as the width of the cavity is at least slightly wider than the width of the interface end of circuit connector 9. For example, cavity 33 may be completely rectangular with dimensions slightly larger than the corresponding dimensions of the interface end of circuit connector 9.

Figure 3E:
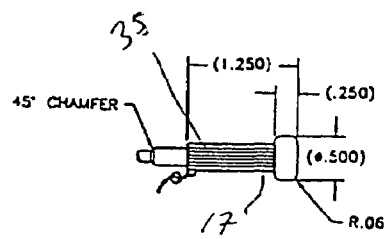
FIG. 3E is a fragmented view of the handle portion of the insertion rod.

As shown in FIGS. 3C and 3E, handle 17 includes ribs 35 on an outer surface thereof to improve gripping. Ribs 35 improve the user's ability to turn insertion rod 7 when attaching sensor 11 to the baby.

B. Shaft

1. Bumps

Shaft 19 is attached to handle 17 and includes a plurality of rings or bumps 37 along its length. When turning insertion rod 7, the surface of shaft 19 may come in contact with the inside surface of introducer tube 5. Bumps 37 reduce the amount of surface area of shaft 19 that touches introducer tube 5, thereby reducing friction between the shaft and the introducer tube. Bumps 37 also center shaft 19 relative to introducer tube 5. Thus, bumps 37 allow insertion rod 7 to be turned with less resistance when attaching sensor 11 to the baby. Preferably, the diameter of bumps 37 is sufficiently less than the inner diameter of introducer tube 5 to allow the circuit connector to fit therebetween and to readily slide in and out of introducer tube 5 along with insertion rod 7.

2. Ramp-shaped Tab

As shown in FIG. 3A, shaft 19 includes a tab 39, which is preferably ramp-shaped, located a short distance from handle 17 and offset approximately 180 degrees relative to tab 13. See FIG. 3F. Tab 39 provides an opposing force for tab 13, such that when tab 13 is inserted inside introducer tube 5, the opposing force increases the tension keeping insertion rod 7 in place. The height of tab 39, measured from a center axis of shaft 19, should be at least slightly larger than the inner radius of introducer tube 5 but less than the inner diameter of introducer tube 5. The height of tab 39, for example, is preferably 0.1 inches plus 0.0625 inches (half of the diameter of 0.125 inches of shaft 19 from FIG. 3C) for an overall height from the center axis of shaft 19 of approximately 0.163 inches, while the inner radius of introducer tube 5 is approximately 0.123 inches (half of the inner diameter of 0.246 inches of introducer tube 5). Thus, when shaft 19 is inserted in introducer tube 5, tab 39 contacts the inside surface of introducer tube 5 and presses that portion of shaft 19 slightly off center away from the point of contact and generally toward tab 13 so that when tab 13 is tucked inside introducer tube 5, insertion rod 7 is securely held in place by the opposing forces. Preferably, tab 39 is ramp-shaped, tapering toward the applicator end of shaft 19 so that tab 39 does not obstruct the insertion of insertion rod 7 into introducer tube 5.

Tab 39 provides a further advantage of helping to prevent circuit connector 9 from becoming twisted inside introducer tube 5. By providing tab 39 on an appropriate side of circuit connector 9, depending on whether insertion rod 7 is turned clockwise or counter-clockwise to attach the sensor, tab 39 pushes circuit connector 9 in the direction of the turning. Because tab 39 contacts the inside surface of introducer tube 5, if circuit connector 9 becomes snagged and starts to twist when the user turns insertion rod 7, tab 39 contacts circuit connector 9 and helps to prevent it from twisting.

C. Applicator

Insertion rod 7 includes an applicator 21, which holds sensor 11 until sensor 11 is detached from insertion rod 7. See FIGS. 3G-3I. Applicator 21 has several features that allow it to (1) securely hold the sensor, (2) provide over-torque protection when attaching sensor 11 to the baby and (3) be readily pulled off of sensor 11 after the sensor has been attached.

1. Hexagonal Shape

Figure 3G:
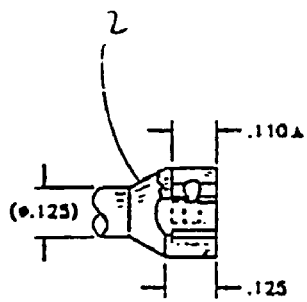
FIG. 3G is an enlarged view of the distal end of the insertion rod showing details of an applicator.
Figure 3H:
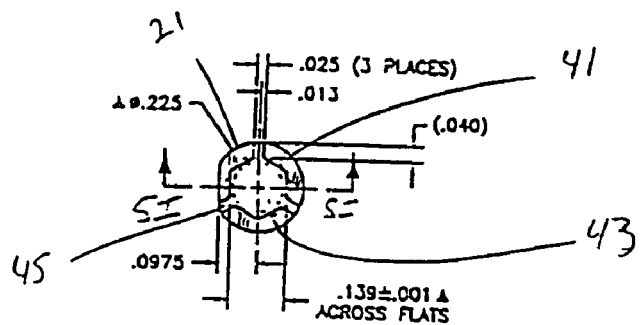
FIG. 3H is an end view of the insertion rod from the applicator end.

As shown in FIG. 3H, applicator 21 includes walls 41 that form a generally hexagonal-shaped opening 43 that mates with a generally hexagonal-shaped base of sensor 11. The hexagonal shape provides a secure socket/nut type coupling of insertion rod 7 (the socket) to sensor 11 (the nut). Thus, when attaching sensor 11 to the baby, turning insertion rod 7 securely turns sensor 11 with little or no slippage.

2. Groove for Engaging Sensor "Bumps"

To help prevent insertion rod 7 from inadvertently pulling off of sensor 11 before sensor 11 is fully attached, an interior surface of walls 41 includes grooves 47 for engaging bumps (described below) on the faces of the generally hexagonal-shaped base of sensor 11. In the embodiment illustrated in FIG. 3I, grooves 45 are provided on the entire interior circumference of applicator 21 and are slightly wider in the middle of each face of wall 41 than at the edges thereof.

3. Over-torque Protection

After sensor 11 is securely attached to the baby, continued turning of sensor 11 may cause tissue damage at the site of attachment. The sensor system of the present invention provides several features for "over-torque" protection to prevent the continued turning of sensor 11 after the sensor is securely attached.

For this reason, the generally hexagonal-shape of applicator 21 is broken into 3 sections by slots 45. Slots 45 provide over-torque protection by allowing walls 41 to flex outward so that the base of sensor slips against the walls of applicator 21 in the event a torque greater than a predetermined torque is applied on the sensor during insertion, i.e., if insertion rod 7 continues to be turned after sensor 11 is properly attached or otherwise has stopped turning. As shown in FIG. 3H, walls 41 of applicator 21 form six faces with the junction of every other face being broken by slots 45. In addition to providing protection from over-tightening of sensor 11, the hexagonal shape of slots 45 provides audible and/or touch indication that the sensor is securely attached. If insertion rod 7 continues to be rotated after sensor 11 is securely attached, walls 41 first flex to prevent over-tightening of sensor 11, then sensor 11 slips within applicator 21 and walls 41 snap back into place as insertion rod 7 repositions itself on the base of the sensor. This slipping and repositioning produces a snapping sound and/or vibration, which may be heard and/or felt by the user, thereby indicating that the sensor is fully tightened.

III. Circuit Connector

FIG. 4 is a fragmented perspective view of circuit connector 9. FIG. 4 also illustrates a hollow spiral needle 65 and a cup 67 that form a part of sensor 11, both of which are described in detail below. Details of circuit connector 9, including dimensions thereof for an exemplary embodiment of the invention, are illustrated in FIGS. 5A-5D. As shown in FIG. 4, circuit connector 9 has an interface end 49, a sensor end 51, and an interconnect portion 53 for carrying signals from sensor end 51 to interface end 49 via conductors 54, which typically have a minimum width of 0.010 inch and a minimum spacing of 0.010 inch with a margin of 0.02 inch provided between the outermost conductor and the periphery of the circuit connector. Sensor end 51 includes a plurality of contact pads 100 that are typically gold plated to a thickness of 25μ inch over a nickel flash.

Circuit connector 9 is preferably fabricated as a flexible printed circuit, or flex circuit. However, in an exemplary embodiment of the present invention, interface end 49 includes a stiffener 130, or rigid material, such as plastic or fiberglass. Stiffening the proximal end of circuit connector 9 makes is possible to insert that end into an interface device for carrying the signals from the sensor assembly to the monitoring device. An alternative embodiment of the present invention, however, contemplates providing leads directly from conductors 54 to the monitoring device, thereby eliminating the need for an interface.

A. Reducing Motion Artifact

1. Narrow Width of Circuit Near Sensor Cup

As shown in FIG. 4, the width of a portion 132 of circuit connector 9 near sensor end 51 is narrower than a portion 134 adjacent thereto to improve its flexibility near sensor end 51, thereby reducing motion artifact. In other words, the adverse effects of small movements of sensor 11 on circuit connector 9 are minimized because the narrowed portion of circuit connector 9 near sensor end 51 readily bends and twists without imparting this bending and twisting along the entire length of circuit connector 9.

2. Slitting Circuit Along its Length

Conductors 54, which are preferably made of copper, are provided along the length of circuit connector 9. The present invention further contemplates providing slits (not shown) between some or all conductors 54 illustrated in FIGS. 5A and 5B, and along the entire length or a portion of the length of the circuit connector. These lengthwise slits improve the flexibility of the circuit connector to reduce motion artifact.

B. Reducing Noise

1. Shielding Circuit

As shown in FIGS. 5C and 5D, a silver shield layer 55 and 57 is provided on each side of conductors 54 along a portion of the length of circuit connector 9. Shield layers 55 and 57 cover the width of circuit connector 9 and are connected to one another through a hole 59 in interface end 49. Hole 59 is typically 0.030 in diameter and is filled with silver ink epoxy to connect shield layers 55 and 57. Shield layers 55 and 57 provide protection from external electrical interference and also from internal electrical interference between signals carried on conductors 54. Thus, shield layers 55 and 57 reduce noise in the sensor system and improve accuracy.

2. Differential Drive for LED

One embodiment of the present invention contemplates differentially driving the LEDs in sensor 11, so that the signal pulses provided to the LEDs in a pair of conductors are equal and opposite one another. Using a differential drive for the LEDs improves low noise performance and permits conductors 54 to be located close together on circuit connector 9 because the signals on the two lines tend to cancel out one another. Safety is also improved by using a differential drive.

C. Exposed Conductor Near Sensor

An exposed conductor 61 is provided near sensor end 51 of circuit connector 9 to serve as a reference electrode that contacts the mother's body, usually internally, when sensor 11 is attached to the baby. Reference electrode 61, as shown in FIG. 5A, is preferably exposed for about 1.0 inch, but a shorter or longer exposed length may be used. Providing an exposed electrode on the circuit connector, rather than on sensor 11 as done in a conventional device, minimizes the size of the sensor while maximizing the likelihood that the reference electrode will have a good contact with the mother. Furthermore, providing a longer exposed length increases the likelihood that at least a portion of reference electrode 61 will make a good contact with the mother.

D. Interface End

Interface end 49 of circuit connector 9 includes contact pads 63a-63g for interfacing with diagnostic equipment (not shown) in a simple and cost-effective manner. For example, circuit connector 9 may be readily adapted to interface with diagnostic equipment via an interface connector 10 as shown in FIG. 6.

IV. Interface Connector

Figure 6:
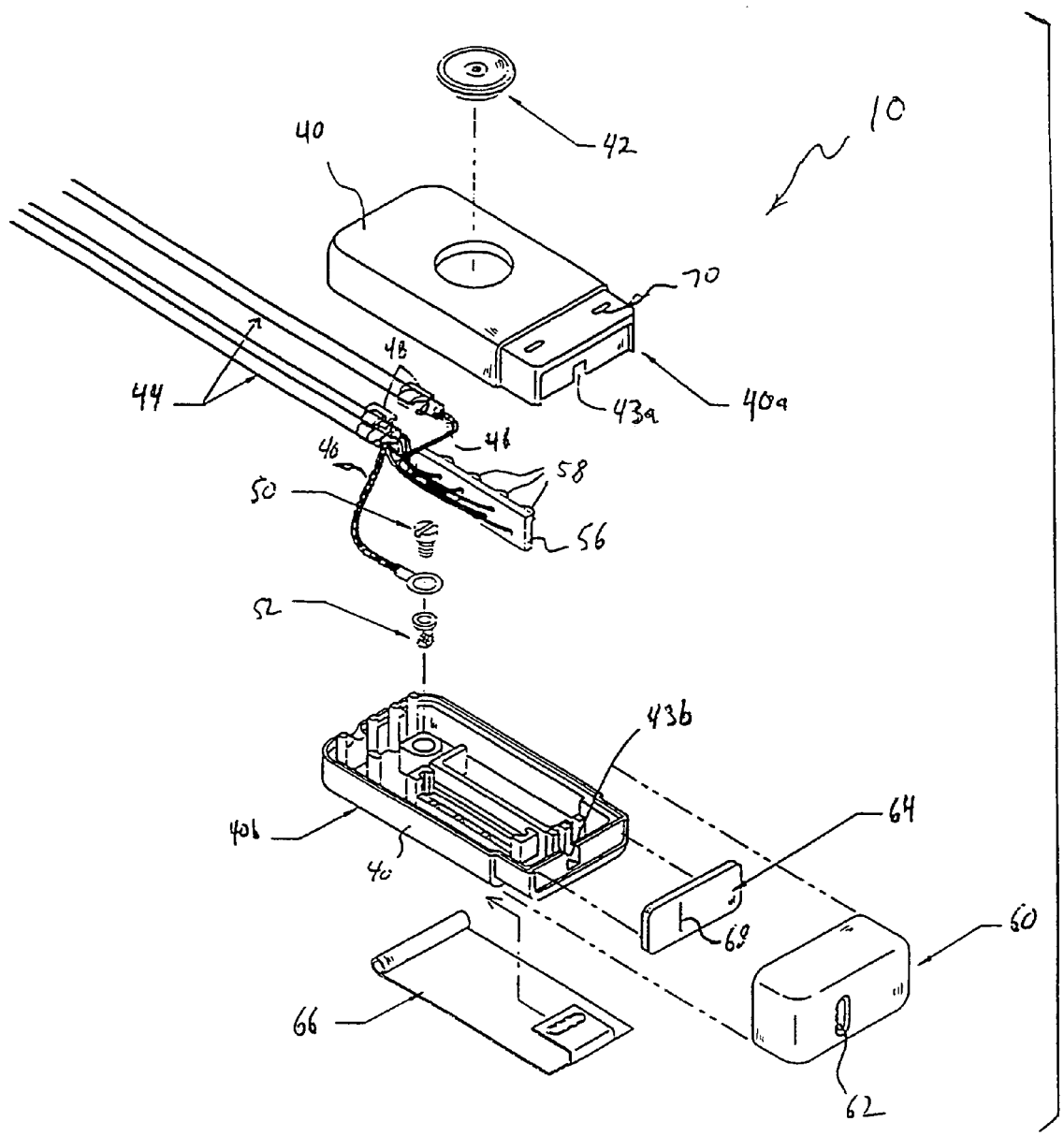
FIG. 6 is a perspective view of a connector for interfacing the sensor system to diagnostic equipment.

As shown in FIG. 6, interface connector 10 includes a housing 40 defined by a top shell 40a and a bottom shell 40b. Preferably, top shell 40a is secured to bottom shell 40b by gluing or ultrasonic welding. However, other methods of securing the two shells may be used, such as screws. A snap button 42 is attached to the top shell 40a, preferably by gluing or ultrasonic welding. Snap button 42 secures connector 10 near the patient during use of the sensor system. For example, a strap may be provided with a mating snap that can be fitted around the mother's thigh so that snap button 42 of connector 10 could be snapped into the mating snap. Alternatively, connector 10 can include a clip 66 for attaching connector 10 to a convenient location on or near the patient. For example, clip 66 could be slipped over a strap, e.g., without the mating snap fitted around the mother's thigh.

Cables 44 enter housing 40 through openings formed when top shell 40a and bottom shell 40b are joined. Cables 44 carry wires 46. Preferably, cables 44 have stress relief tabs 48 near the end thereof where wires 46 emerge. Stress relief tabs 48 are located inside housing 40 when assembled, so that stress on cables 44 is not imparted to wires 46. Wires 46 may include a ground wire secured to the housing via a screw 50 threaded into a threaded insert 52, the threaded insert 52 being attached to bottom shell 40b. Preferably, the ground wire provides a ground connection for shield layers 55 and 57.

Wires 46 connect to a connector board 56 having conductive contacts 58. Housing 40 secures connector board 56 in place and in proper position for making electrical contact between contact pads 63a-63f, shown in FIG. 4, and conductive contacts 58 when interface end 49 of circuit connector 9 is attached to connector 10. In addition, a conductive contact provides a ground connection from ground wire 46 to shield layers 55 and 57 via plated through hole 59.

Connector 10 includes an end cap 60 having an opening 62 aligned with corresponding slots 43a, 43b formed in top shell 40a and bottom shell 40b. Connector 10 further includes a seal 64 having a slit 68 also aligned with opening 62. Seal 64 is made from a resilient material so that slit 68 expands to accommodate interface end 49 of circuit connector 9 when inserted through opening 62. Seal 64 covers the opening in housing 40 and protects connector board 56, conductive contacts 58, and interface end 49 from moisture and other environmental disturbances during use. Seal 64 is preferably made of neoprene and fits in a shoulder formed by housing 40. The seal 64 is held in place by end cap 60. End cap 60 is removably secured to housing 40 in a snap-fit manner by grooves 70 in housing 40, which mate with corresponding bumps (not shown) on end cap 60. End cap 60, however, may also be glued or ultrasonically welded to housing 40. Alternatively, housing 40 may be formed without an end cap, with seal 64 held in place within housing 40.

Preferably, interface end 49 of circuit connector 9 is frictionally held in place by conductive contacts 58a-58g and seal 64. However, mechanisms, such as a snap-fit assembly or pin, can be provided on interface end 49 and/or connector 10 to hold interface end 49 of circuit connector 9 in place.

V. Sensor

As shown in FIG. 4 and discussed above, sensor 11 includes a hollow spiral needle 65 and a cup 67. In the illustrated embodiment, needle 65 includes an LED circuit 69 and a photodetector circuit 71. Signals are provided to LED circuit 69, which produces light that is transmitted through the patient and received by photodetector circuit 71. The signals indicative of the received light are returned from photodetector circuit 71 to the diagnostic device via circuit connector 9. Details of cup 67, as well as dimensions thereof according to a preferred embodiment of the present invention, are shown in FIGS. 7A-7E. Details of needle 65, as well as dimensions thereof according to a preferred embodiment of the present invention, are shown in FIGS. 8A-8L. It is to be understood that the functions of emitting and receiving light from the needle can be accomplished via optical fiber, with the light source and light detectors being provided at a location outside the needle.

A. Cup

Cup 67 holds needle 65 and couples it to applicator 21 of insertion rod 7 when attaching sensor 11 to the baby. Cup 67 is made of, for example, a biologically compatible plastic, and preferably is a 10% fiberglass filled polycarbonate, such as GE Lexan 500. Preferably, before assembly, cup 67 is annealed for about 15 minutes at approximately 100° C. Cup 67 should be left in the oven for about 3-4 hours after annealing, to allow the cup to cool slowly.

1. Hex Shape of Base

Figure 3I:
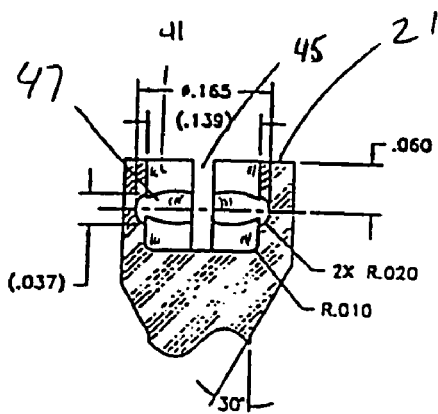
FIG. 3I is a sectional view taken along section line 3I-3I in FIG. 3H.

Cup 67 has a generally hexagonal-shaped base 73 that matches the generally hexagonal-shaped opening 43 of applicator 21 (see FIGS. 3G-3I). The hexagonal shape of the female portion of applicator 21 receives the hexagonal-shaped base 73 and facilitates a secure socket/nut type coupling of insertion rod 7 (the socket) to sensor 11 (the nut). Thus, when attaching sensor 11 to the baby, turning insertion rod 7 turns sensor 11 with little or no slippage until the sensor is securely attached.

2. Rounded Edges for Over-torque Protection

As discussed above, after sensor 11 is securely attached to the baby, continued turning of the sensor may cause tissue damage at the site of attachment. To provide over-torque protection, edges 75 of base 73 are rounded, for example, as shown in FIG. 7C, to a radius of about 0.022 inches. Rounded edges 75 allow base 73 to "slip" in applicator 21 when an over-torque is applied to cup 67, which typically may occur after sensor 11 is securely attached.

3. Bumps for Retaining the Cup in the Applicator

As shown in FIGS. 4 and 7A-7D, opposing faces of base 73 have raised bumps 77 provided thereon. Bumps 77 engage grooves 47 when base 73 is inserted into applicator 21 to help prevent insertion rod 7 from inadvertently pulling off of sensor 11 before sensor 11 is fully attached to the baby. Bumps 77 increase the "pull-off" force needed to disengage insertion rod 7 from sensor 11. Preferably, the pull-off force is optimized to avoid tissue damage to the baby while sensor 11 remains engaged with the baby, but permits sensor 11 to disengage from applicator 21 as insertion rod 7 and introducer 5 are removed from the patient leaving sensor 11 and when sensor 11 is in place on the baby.

4. Assembly Features for Holding Needle

Cup 67 is formed with a recessed groove 79 for holding needle 65 in place during final assembly. Groove 79 has a spiral shape corresponding generally to the spiral shape of the needle. As hereinafter discussed with respect to the final assembly of sensor system 1, needle 65 is preferably not threaded into recessed groove 79. Rather, needle 65 is positioned inside cup 67 above groove 79 at a desired orientation and then snapped into recessed groove 79.

5. Opening for Receiving Circuit Connector

Cup 67 has an opening 81 in the side for receiving sensor end 51 of circuit connector 9. By providing only a slit-like opening in the side of cup 67 into which the circuit connector inserts, the present invention substantially maintains the general configuration of cup 67 thereby achieving several beneficial results. For example, the natural shape of cup 67 facilitates holding a bonding adhesive therein better than if the side of the cup were open to receive circuit connector 9 as is the case with some conventional sensors. Also, there is a larger bonding area for the needle than if the side of the cup were open. Finally, using only the slit-like opening provides a 360° area against which the needle can be bonded.

Preferably, opening 81 is formed near the bottom of cup 67, see in FIGS. 7A-7B, so that when sensor end 51 of circuit connector 9 is inserted through opening 81, sensor end 51 is adjacent and generally parallel to the bottom of cup 67. The portion of circuit connector 9 proximate to sensor end 51 bends to be generally perpendicular to the bottom of cup 67 and sensor end 51 when the assembled sensor and circuit connector assembly are disposed in introducer tube 5. For this reason, it is preferable that the width of sensor end 51 of circuit connect be as narrow as possible to provide a smooth bend while minimizing the chance of kinking caused by bending the relatively flat circuit connector over the curved edge of the cup.

B. Needle

As shown in FIG. 4, needle 65 houses LED circuit 69 and photodetector circuit 71 and has several features that help sensor 11 remain attached to the patient without significantly increasing tissue trauma and application torque and without significantly increasing removal resistance. Needle 65 is described in detail with respect to FIGS. 8A-8G. Needle 65 is formed in several distinct stages, referred to as a "J" stage, a "P" stage, and an "O" stage, with various procedures performed at each stage. The use of these stages, as also described, allows needle 65 to be manufactured effectively, reliably, and with a low dropout rate.

1. Bumps

Figure 8A:
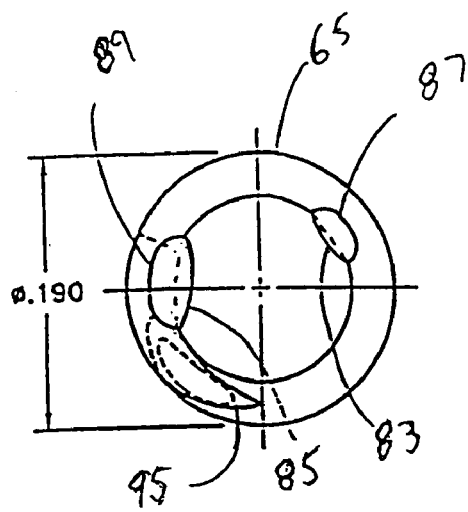
FIG. 8A is a top view of the needle portion of the sensor.

Referring to FIG. 8A, needle 65 preferably includes bumps 83 and 85, an LED window 87, and a photodetector window 89. Bump 83 is formed in the region of LED window 87 and bump 85 is formed in the region of photodetector window 89. For example, the LED and photodetector windows 87 and 89 may be slightly overfilled with a transparent potting material to respectively form bumps 83 and 85, which help hold the needle in place without significantly increasing tissue trauma, application torque, or removal resistance. Needle 65 preferably includes two bumps formed on an inner surface of the spiral. However, different numbers and locations of bumps may be used. Also, other methods of forming the bumps also may be employed. For example, a single bump may be provided on an outer surface of the spiral. The bump may be formed by machining the needle material to cause a bulge in the material.

2. The "J" Stage

Needle 65 begins as a straight piece of tubing and is preferably formed from a precut length of tubing with an inner diameter of about 0.19 inches, an outer diameter of about 0.3 inches, and a length of about 1.13 inches. Preferably, the material for tubing 91 is 21½ RW 304 stainless steel, full hard hypodermic needle tubing. Other dimensions and materials may also be used, but, preferably, according to the invention, a relatively large gauge tubing is used to facilitate needle 65 better, more reliably, and reproducibly staying in the tissue. A mandrel is used to form the tubing into a spiral. However, as discussed above, the forming occurs at various stages. The "J" stage includes forming the tubing into a "J" shaped needle.

With a mandrel secured in the vise, one end of the tubing is clamped on the mandrel. The top of the tubing is pressed with an aluminum plate while turning the mandrel so that the tubing makes a 180° turn, thereby forming the "J" shaped needle. Thereafter, the clamp may be removed and the "J" shaped needle may be taken off the mandrel.

3. Multi-plane Beveling

A tip 95 of needle 65 is formed by a multi-plane beveling process to ensure sharpness and strength of the needle. Preferably, the beveling process includes forming at least three facets. A first facet 92 is shown in FIG. 8C, and a second facet 94 and third facet 96 are shown in FIG. 8D. Each of the facets may be formed by hand grinding tip 95 to the desired respective angles. Preferably, as described below, the first and second facets are formed using needle holding fixtures and grinding fixtures with predetermined stop positions, and the third facet is formed by hand grinding.

a. First Facet

As is illustrated in FIG. 8C, first facet 92 is cut at angle of approximately 15° with respect to a plane of the spiral near tip 95 of the needle. A first facet grinding fixture includes a holding fixture configured to hold the needle securely and in an appropriate position for grinding the needle to the desired shape. In a further embodiment of the present invention, facet 92 is beveled into still further facets to increase the strength of the tip of needle 65. For example, the most distal portion of facet 92 may be provided with 30° angle, followed by a 20° angle, and finally a 15° defining the remaining portion of facet 92.

"J" shaped needle 93 is placed in the holding fixture of the first facet grinding fixture. A mister is set up to mist onto the "J" shaped needle and the grinding wheel at all times during grinding. The holding fixture is pre-configured with a stop at the desired amount of beveling. A Dremel motor is turned on to full speed and the "J" shaped needle is slowly ground to the point where it hits the stop on fixture. Any burrs in the bevel may be removed with the utility knife, razor blade, or file or the like.

b. Second Facet

The "J" shaped needle with first facet 92 is placed in the holding fixture of second facet apparatus, which has a stop for the desired amount of grinding. The Dremel tool is set to speed 1, less than the full speed, and turned on. The grinding wheel is positioned against the "J" shaped needle in the location for second facet 94 and grinds the "J" shaped needle until it hits the stop.

c. Third Facet

The "J" shaped needle with first and second facets 92 and 94 is held with hemostats or tweezers at the junction of the curved and straight portions. A Dremel tool, for example, is used, preferably with the fine grinding wheel, to grind third facet 96 on inside curved end of needle and, if necessary, to touch up first facet 92 and second facet 94. Preferably, the bevel is about 0.100 inches ±0.010 inches.

4. The "P" Stage

Figure 8B:
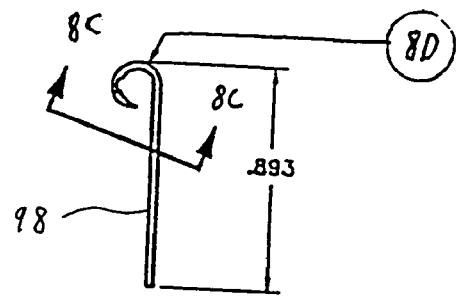
FIG. 8B is a side view of the needle in a "J" stage of manufacturing.

The "P" stage includes forming "J" shaped needle into a "P" shaped needle 98, as shown in FIG. 8B. With the mandrel in the vise, the "J" shaped needle is clamped on the mandrel under the clamp. The clamp should not be placed directly on tip 95. The straight portion of the "J" shaped needle is pressed with the aluminum plate while turning the mandrel so that the "J" shaped needle makes about a 90° turn, thereby forming "P" shaped needle 98. Thereafter, the clamp may be removed and "P" shaped needle 98 may be taken off the mandrel.

5. Window Forming

Figure 8G:
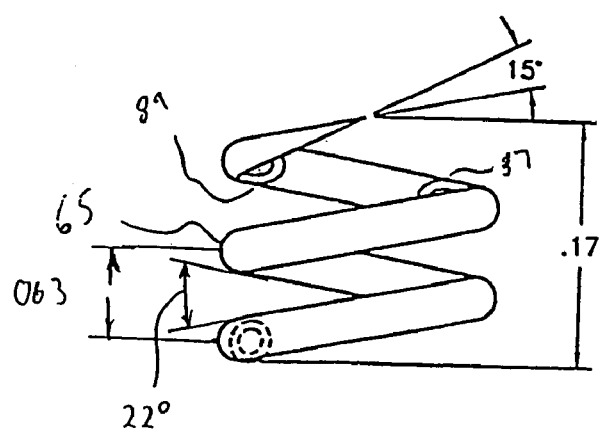
FIG. 8G shows the needle in an "O" stage of manufacturing.
Figure 8C:
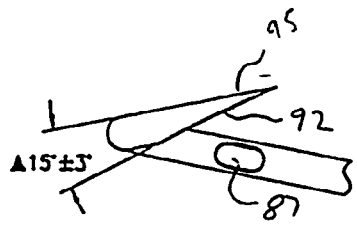
FIG. 8C is an enlarged view taken along line 8CB-8C in FIG. 8B.
Figure 8D:
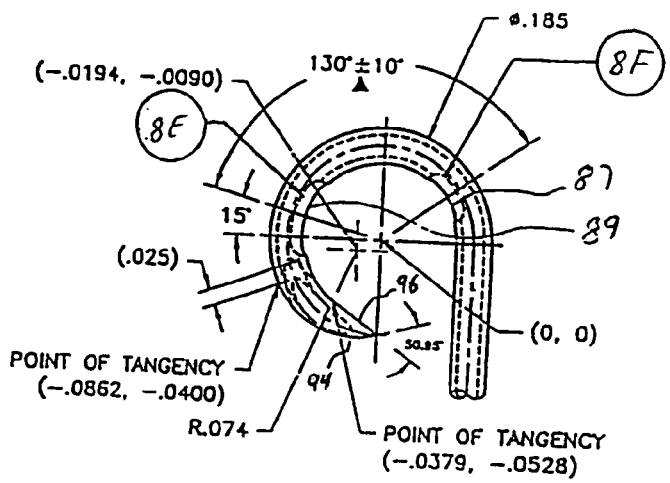
FIG. 8D is a top view of the needle in a "P" stage of manufacturing.
Figure 8E:
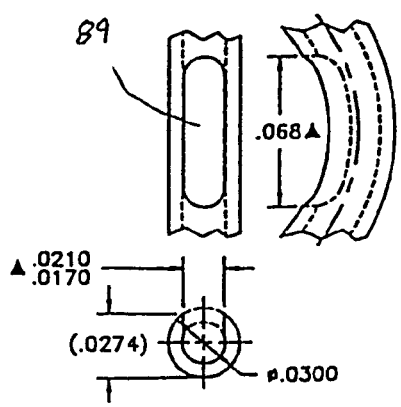
FIGS. 8E and 8F are enlarged views showing details of the needle windows.
Figure 8F:
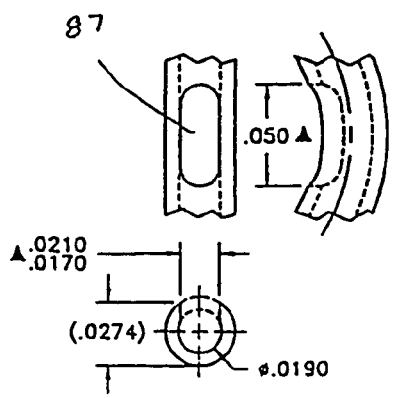

As shown in FIG. 8D, the needle is formed with LED window 87 and photodetector window 89. Photodetector window 89 is preferably provided as near as possible to the beveled end (tip) of needle 65 and the center of LED window 87 is also preferably provided as close as possible to the beveled end of needle 65 while still providing a direct line of sight between the two windows. It is preferable to locate the windows as close as possible to the beveled end of the needle to ensure that light is transmitted between the two windows even if the needle is not fully inserted within the patient. In a preferred embodiment of the present invention, the center of LED window 87 is offset from the center of photodetector window 89 about 130°±10°. The details of photodetector window 89 and LED window 87 are shown in FIGS. 8E and 8F, respectively. In a preferred embodiment of the present invention, windows 87 and 89 are formed in the needle by grinding the needle material away. Other methods, however, may be used, including chemical etching.

To form windows 87 and 89, a needle holding fixture is placed in the bottom position of the grinding apparatus with the fixture angled upward. A lever of the fixture is turned to the down position and the clamp is loosened. A mineral oil mister is positioned to mist on "P" shaped needle 98 and the end mill. Preferably, a microscope is positioned to view the needle well.

In the needle holding fixture there are two possible needle positions. "P" shaped needle 98 should be placed in the fixture so that the non-beveled end of needle is pointing toward the operator. "P" shaped needle 98 must rest on the front locator pin. Once positioned, the needle can be clamped into the fixture with the thumb screw. The thumb screw should be tightened snugly and the flow of mineral oil mist is then initiated. The servo motor is then turned on and the end mill is lowered. Once the end mill is lowered, the lever on the fixture is lifted to the full up position, thereby cutting window 89. After window 89 is cut, the end mill is raised, the needle clamp is released, and needle is removed. Window 89 should be cut on the inside of the helical curve beginning about 0.010 to 0.015 inches from the proximal end of the bevel, as shown in FIG. 8G. Preferably, the dimensions are measured with pin gauges or a microscope reticule.

The procedure for cutting LED window 87 is similar to the above-described procedure for cutting photodetector window 89. However, the needle sits in a different position during the milling process. For LED window 87, "P" shaped needle 98 is placed in the fixture so that the non-beveled end of the needle is pointing away from the operator. As discussed above and shown in FIG. 8D, the center of LED window 87 should be about 130 degrees from the center of the photodetector window 89. Preferably, the dimensions are measured with the pin gauges or a reticule and the angle is measured with the angle template or angle reticule.

6. Deburring and Cleaning

In preparation for final assembly, "P" shaped needle 98 is preferably deburred and cleaned. A razor blade is used to trim off all large protruding burrs from the surface of windows 87 and 89. The tail end (non-beveled) is checked to make sure that the end of the needle is open. If the end is blocked or has burrs, the tip of the razor blade is used to deburr the end. The Foredom drill and a coarse diamond bit is used to remove burrs from inside and outside of windows. Preferably, all burrs are removed.

The deburred "P" shaped needle 98 is then placed in the ultrasonic cleaner and cleaned for about 30 minutes in a solution of distilled water and 2% micro cleaning solution. "P" shaped needle 98 is then removed and the solution in ultrasonic cleaner is replaced with 100% distilled water. "P" shaped needle 98 is again placed in the ultrasonic cleaner and cleaned for about 15 minutes and thereafter removed and compressed air is blown through "P" shaped needle 98.

A microscope reticule and/or pin gages are used to measure all critical dimensions, which include the angle or angles of the first facet, the angle between the centers of windows 87 and 89, and the respective lengths and widths of photodetector window 89 and LED window 87. The width of LED window 87 and photodetector window 89 should be between about 0.0170 inches and 0.0210 inches. The length of photodetector window 89 should be about 0.068 inches, and the length of LED window 87 should be about 0.050 inches. Preferably, after cleaning, the "P" shaped needle is inspected for any damage or remaining burrs. The dimensions identified as critical are so identified because of the parts, materials, and circuits used in the preferred embodiment. It is to be understood that other part, material, or circuit choices may require different "critical" dimensions.

FIGS. 8A and 8G illustrate preferred dimensions of needle 65, which include an overall outer diameter of about 0.190 inches and an overall depth of about 0.170 inches. As shown in FIG. 8G, the spiral preferably has a pitch of about 0.063 inches and spirals at an angle of about 22°. As hereinafter discussed with respect to final assembly, the final needle wrap preferably occurs after LED circuit 67 and photodetector circuit 71 have been inserted in the needle.

C. Sensor Circuits

FIGS. 9A and 9B are perspective views of LED circuit 69 and photodetector circuit 71, respectively. As shown in FIG. 9B, photodetector circuit 71 includes a photodiode die 97 mounted on a flexible circuit board 99. A wire bond 101 connects a bond pad on one side of photodiode die 97 to a bond pad 103 on flexible circuit board 99. The other side of the photodiode die 97 is directly connected to a large die attach pad 105 on the flexible circuit board 99. A suitable photodiode die 97 is provided by Silicon Sensors, Inc., in Dodgeville, Wis., part number 5538A800.

LED circuit 67 includes two LED chips 107 and 109 mounted on a flexible circuit board 111. See FIG. 9A. A wire bond 113 connects a bond pad on one side of first LED chip 107 to a bond pad 115 on flexible circuit board 111. A wire bond 117 connects the first LED chip 107 to second LED chip 109. The other sides of the two LED chips 107 and 109 are directly connected to a large die attach pad 119 on the flexible circuit board 111. In FIG. 9A, LED chip 107 is shown as being taller than LED chip 109. However, the actual heights of LED chips 107 and 109 vary depending on the manufacturer. LED chip 107 preferably produces light with a wavelength of about 730 nm. A suitable first LED chip 107 is provided by Mitsubishi Cable America, Inc., in New York, N.Y., with a part number MC-R1N-DD730/5. LED chip 109 preferably produces light with a wavelength of about 940 nm. A suitable second LED chip 109 is provided by Mitsubishi Cable America, Inc., in New York, N.Y., with a part number ED-012 IRA. Wire bonds 101, 113 and 117 are attached using the Shinkawa Ultrasonic Wedge Bonder.

In a preferred embodiment of the present invention, flexible circuit boards 99 and 111 include a layer of polymide about 0.0010 inches thick, an adhesive layer about 0.0010 inches thick, a layer of copper (corresponding to the conductors) about 0.0007 inches thick, another adhesive layer about 0.0005 inches thick and generally conforming to the shape of the copper layer, and another layer of polymide about 0.0010 inches thick and generally conforming to the shape of the preceding adhesive layer.

1. Threading Circuits into Needle

According to the invention, LED circuit 69 and the photodetector circuit 71 are threaded into needle 65 in a manner, hereinafter described in detail, which minimizes the potential for damaging the circuits. In particular, photodetector circuit 71 is threaded into needle 65 before LED circuit 69 because photodetector window 89 is nearest to the beveled end of needle 65. Preferably, a microscope is used to visually follow the procedure.

"P" shaped needle 98 is held in a needle holding fixture while threading photodetector circuit 71 in through photodetector window 89 with tweezers. After the end of photodetector circuit 69 shows out of the non-beveled end of "P" shaped needle 98, circuit 71 may be grasped and pulled to position wire bond 105 near window 89. With one side of a tweezers, the wire bond end of the photodetector circuit is dipped into window 89 by pressing photodiode die 97 near wire bond 105. Then, the back of photodiode die 97 is pushed forward into window 89 with the other end of the tweezers. This will cause photodetector circuit 69 to drop down into window 89 without damaging wire bond 105. The wire bonds should not be pressed on directly, because it may break. The top of photodiode die 97 should be pressed on carefully because it will tend to break also. Preferably, after circuit 71 has dropped into the window, the end is grasped and used to center photodiode die 97 in window 89. Photodiode die 97 is then held against the bottom of the needle while applying one drop of UV adhesive Dymax 1-20280 between photodiode die 97 and the wall of "P" shaped needle 98. The adhesive should cure for about 5 seconds with a UV lamp while holding photodiode die 97 in place. Then, the needle is tested for continuity and shorting. Next, LED circuit 67 is threaded into "P" shaped needle 98 using the same procedure except that LED circuit 67 is threaded through LED window 87.

"P" shaped needle is wrapped into the final form "O" (spiral) shape of needle 65, as shown in FIGS. 4, 8A and 8G. This is accomplished by threading the "P" shaped needle onto a mandrel for clamping the needle about 300° from the beveled end. This ensures that neither LED window 87 nor photodetector window 89 is clamped. Then, the mandrel is oriented so that the beveled end of the "P" shaped needle points upward. An aluminum plate is held on top of the mandrel and the mandrel is turned to wrap the needle around it to form the "O" shaped needle 65. Pliers are used to finish rounding the end of needle 65 so that there are no straight sections. Excessive force should be avoided as it may crush needle 65 and/or cut circuits 69 and 71. Preferably, the final "O" shape for needle 65 makes just over 2 full turns after the final wrap.

VI. Final Assembly

After each of the above described sub assemblies are complete, sensor system 1 is ready for final assembly. First, circuit connector 9 is attached to cup 67. Cup 67 is placed in the final assembly fixture with opening 81 aligned with the flat facet of the fixture. Sensor end 51 of circuit connector 9 is slid through opening 81 in cup 67 with the conductive pads facing up. Circuit connector 9 is aligned so that it exits perpendicular to cup 67. Sensor end 51 is lifted up inside cup 67 and a dab of UV adhesive Loctite 3321 is placed on the floor of cup 67. Sensor end 51 is then pressed onto the adhesive and held down firmly with tweezers while curing the adhesive with a UV lamp.

Needle 65 is then snapped in cup 67 so that the ends of circuits 69 and 71 are positioned in the cup with the conductors pointing upward, through the opening in the top of cup 67 so that the photodiode circuit 71 is on the left (i.e. at the 6:00 position in FIG. 4). Needle 65 is turned, without yet snapping it into place, with tweezers counter clockwise until the non-beveled end of needle 65 is in about the 11:00 position in FIG. 4. Then, holding needle 65 with tweezers, the needle is pushed into cup 67 until it snaps into recessed groove 79.

Next, the electrical connections between circuit connector 9 and LED and photodetector circuits 69 and 71 are made. LED circuit 67 may be distinguished from the photodetector circuit 71 because the end of LED circuit 69 should be longer that the end of photodetector circuit 71. Photodetector circuit 71 (shorter tail) should be positioned between the third and fourth conductors from the right side of circuit connector 9. LED circuit 69 (longer tail) should be aligned between the two right most conductors of circuit connector 9. Circuits 69 and 71 should then be secured in position around the circuit connector pads by dabbing UV adhesive Dymax 1-20280 on two circuits 69 and 71 at the top and bottom of the large bond pads. The adhesive is then cured with the UV lamp. Both circuits 69 and 71 are then cut to length inside cup 67 using the tip of a sharp razor blade. The needle should be scraped vigorously at the bonding site, (i.e. the entire length of the pad) to ensure good adhesion and a low resistance. Using the utility knife, conductive adhesive Acheson 5915 is applied to make the conductive bonds. The conductive adhesive should have had time to sit in order to ensure a high viscosity. Four conductive bonds are made: one from each conductor of circuits 69 and 71 to the adjoining large pad of circuit connector 9. The scraped portion of needle 65 is conductively bonded to the large bond pad at the 9:00 position shown in FIG. 7. Conductive adhesive should be liberally applied all along the length of this bond pad. Then, the assembled sensor 11 and circuit connector 9 are oven cured for about 20 minutes at about 150° C. Preferably, before the final potting of sensor 11, the electrical properties of the sensor are tested.

If sensor 11 passes the electrical test, the final potting may be applied. The cup is potted by applying adhesive Dymax 1-20280 with a syringe or an EFD dispenser. An applicator needle is used to dab the adhesive into position. The cup is filled ¾ full making sure there are no air gaps and then cured with the UV lamp. The needle should be completely covered at least to the 12:00 position and not past the 10:00 position. Then adhesive Dymax 1-20280 is dabbed into the bevel with an applicator needle until it is filled flat across from edge to edge. As discussed above, each window 87, 89 is potted by dabbing on adhesive Dymax 1-20280 until the window is slightly overfilled. Next the adhesive is cured with the UV lamp using two or three 5 second bursts. A light coat of adhesive Loctite 3321 is placed on the bottom of circuit connector 9 to seal where it enters the cup and cured with the UV lamp. Circuit connector 9 is pulled down so that it lies flat along the cup wall. The gap between the top of circuit connector 9 and cup slot 81 is filled and cured with the UV lamp. This process should make circuit connector 9 and adhesive flush with the cup. Preferably, the final potting should not increase the outer diameter of the cup. The windows should be checked to ensure that there is no roughness in the windows and that the LEDs and wire bonds are visible through the window.

Before inserting insertion rod 7 into introducer tube 5, sensor 11 should be oriented so that circuit connector 9 is on the side of insertion rod 7 with slot 31 in the side of handle 17. After sensor 11 is so aligned, interface end 49 is inserted in a hollow end 33 of handle 17. Next, circuit connector 9 is held against insertion rod 7 so that it lays in slot 31 along handle 17. Insertion rod 7 (with sensor 11 attached thereto) is slid into introducer tube 5 while holding circuit connector 9 in place. When insertion rod 7 is almost fully inserted, tab 13 is held down and slid under introducer tube 5 so that the assembled sensing system is ready for shipping.

VII. Multiple Optical Wavelengths

Optical measurement of light transmission and/or absorption assumes a model of the related physical environment. This model is inherently an approximation of the actual physical environment that results in measurements within acceptable levels of error. Optical measurements from a living subject can be particularly error prone because the modeled environment is variable by subject and also time-varying. Higher error levels are acceptable as long as they generate clinically significant data. As noted above, conventional pulse oximeters have yet to be accepted as the primary diagnostic tool for measuring fetal blood oxygen saturation level during labor and delivery because of low usable signal time and concerns about accuracy. In one embodiment, the optical measurement device of the present invention provides a more accurate measurement by taking measurements at a plurality of different wavelengths and combining sets of measurements based on a more complete model than is possible in conventional pulse oximeters. While the embodiments according to the invention disclosed herein are explained in the contextual example of pulse oximetry, other embodiments can be readily extended to many optical measurements such as, for example, measurement of blood glucose, bilirubin, and hemoglobin.

Conventional pulse oximetry measurements of arterial blood oxygen saturation levels are based on the ratio of the absorption of light by tissue at two distinct wavelengths. For any combination of wavelengths, there are inaccuracies due to the non-exact model for the measurement. For example, the commonly used 660/940 nanometer (nm) wavelength combination returns good pulse signals but is subject to higher sensitivities to factors such as variations in blood-tissue ratio and Hb content. The 660/940 nm combination is also more sensitive to inaccurate LED center wavelengths frequencies (which can vary as much as +/−15 nm for any particular LED). Other wavelength combinations involve similar tradeoffs. For example, using a 730/940 nm wavelength combination results in much less sensitivity to LED inaccuracies but also returns a weaker pulse signal.

One embodiment of the present invention provides at least two sets of wavelengths, with each set containing at least one wavelength that is different from the wavelengths in the other set or sets, to increase the accuracy of the measurement. Two sets of wavelengths, with each set containing a pair of wavelengths, can be achieved, for example, using three LEDs. However, in the embodiment illustrated in FIG. 10, two sets of wavelengths, each set containing a pair of wavelengths, is accomplished using four LEDs, each operating at a different wavelength.

Figure 10:
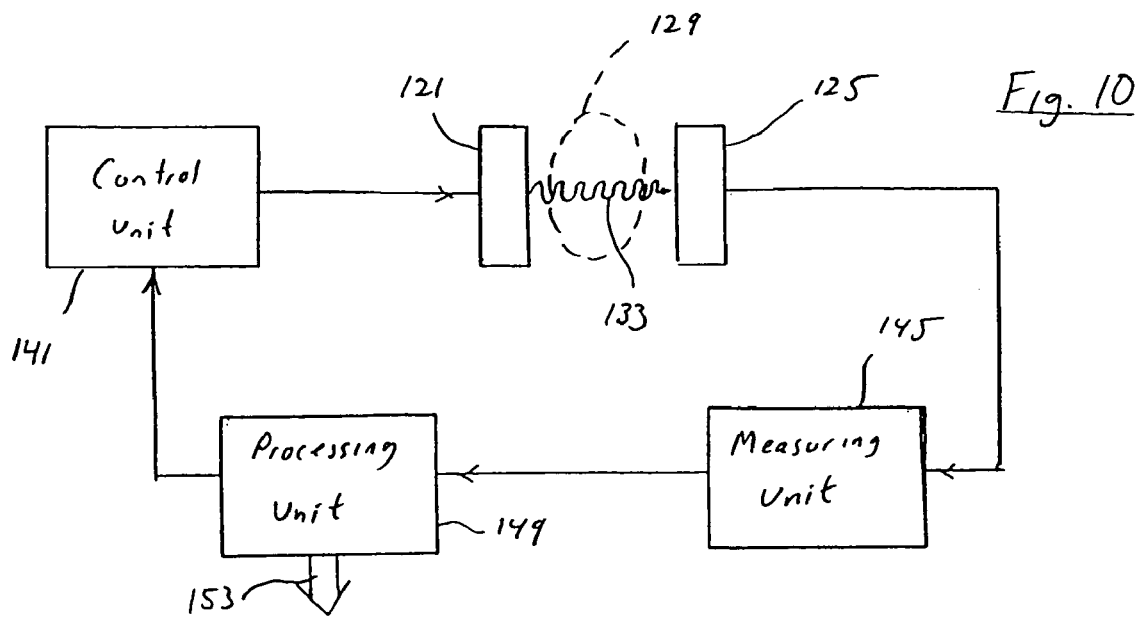
FIG. 10 is a block diagram of an optical measuring device according to the invention utilizing a spectrum of wavelengths.

The embodiment shown in FIG. 10 includes a control unit 141, a light source 121, a light detector 125, a measuring unit 145, and a processor unit 149. Tissue 129 is positioned between or against light source 121 and light detector 125. In this embodiment, light source 121 produces at least 4 wavelengths, $\lambda_1, \lambda_2, \lambda_3$, through $\lambda_n$. Processor unit 149 is coupled to control unit 141 to select a desired one of these wavelengths. Control unit 141 is coupled to light source 121 to activate the desired wavelength. Light source 121 produces light having the desired wavelength, which is then transmitted through the tissue 129 to light detector 125 along optical measurement path 133. Light detector 125 is coupled to measuring unit 145, which measures the light intensity incident on light detector 125. Measuring unit 145 is coupled to processor unit 149, which receives and processes the light intensity measurement to produce measurement 153.

Figure 11:
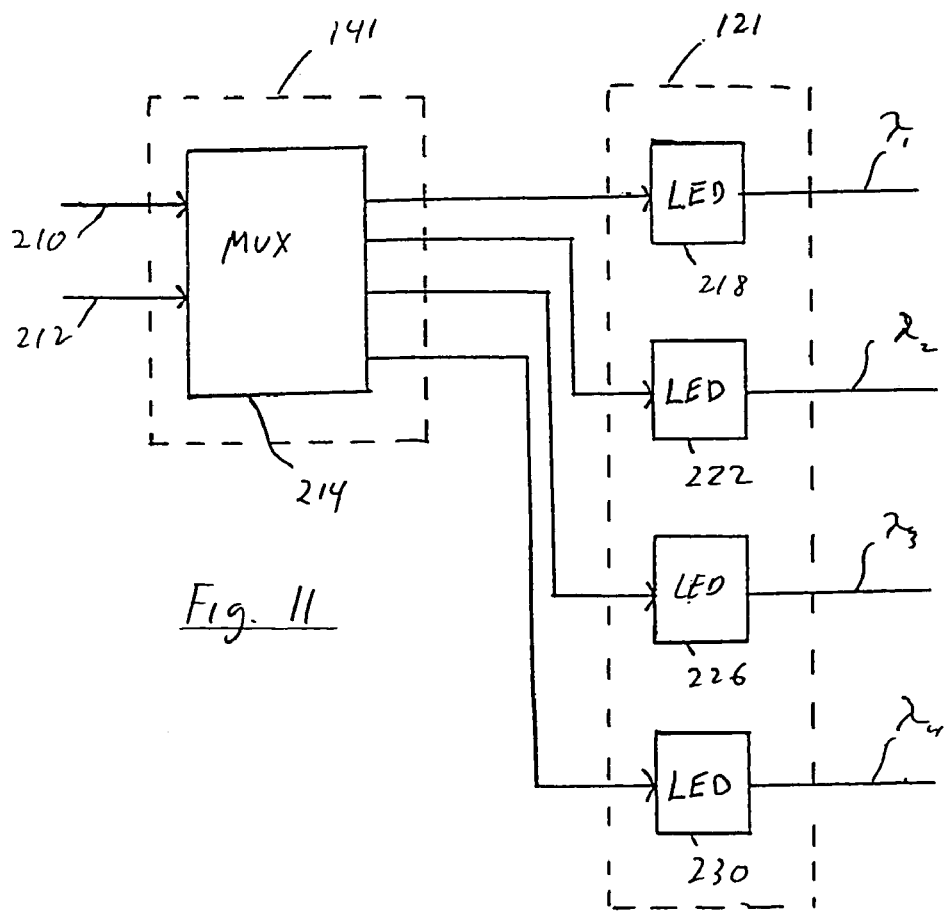
FIG. 11 is a block diagram of a control unit and light emitter according to the invention.

Processor unit 149 selectively requests and receives measurements of the light intensity for any wavelength $\lambda_{1-n}$. For example, FIG. 11 illustrates an embodiment of control unit 141 and light source 122. Control unit 141 includes a multiplexer 214 (MUX) responsive to SEL signal 210 and CS signal 212. Light source 206 includes light emitting diodes (LEDs) 218, 222, 226, and 230 that emit light of wavelengths $\lambda_1, \lambda_2, \lambda_3$, and $\lambda_4$, respectively. CS signal 212 selectively activates MUX 214. When MUX 214 is deactivated, none of the LEDs emit light. When MUX 214 is activated, SEL signal 210 selects which one of the four MUX 214 output signals is activated. The LED coupled to the activated output signal emits light at its corresponding wavelength.

Figure 12:
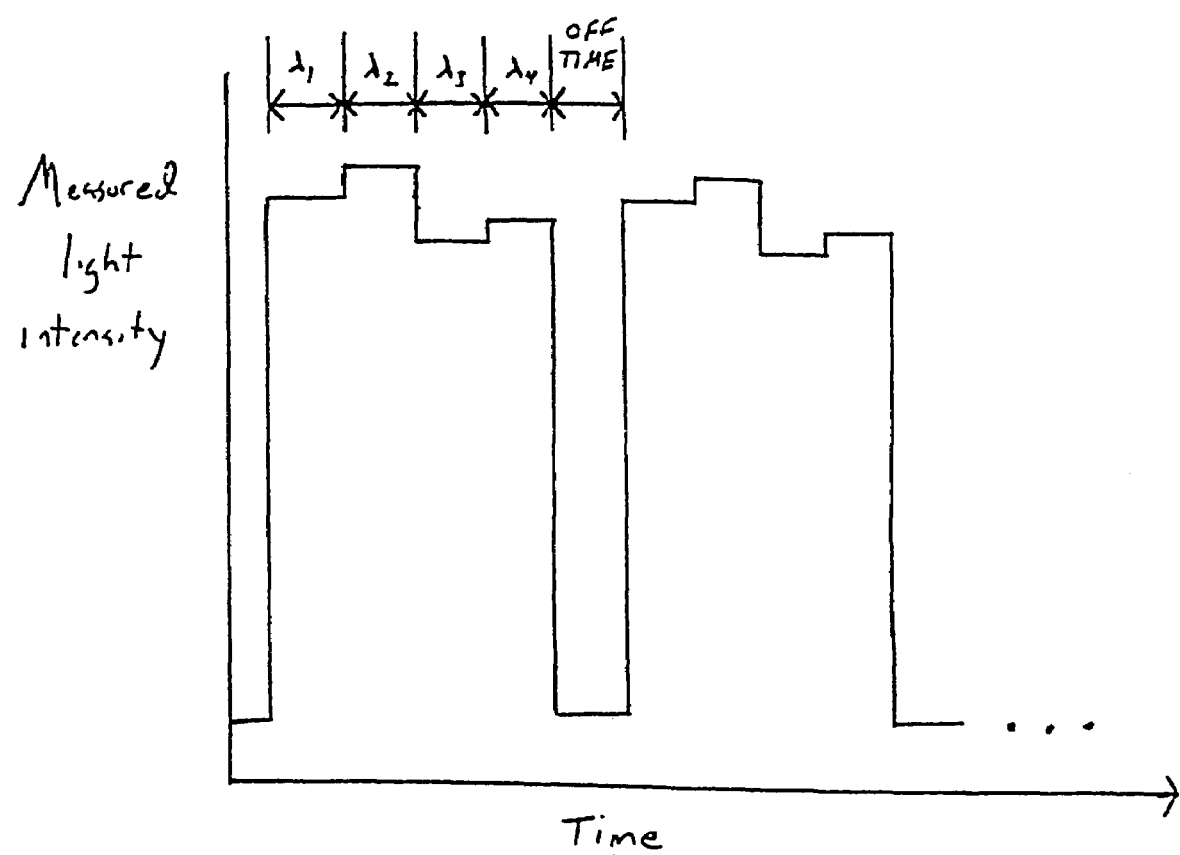
FIG. 12 is a timing diagram of a multiplexed wavelength signal produced by the invention in FIG. 11.

Processor unit 149 utilizes control unit 202 and light source 206 to achieve a time multiplexing of the four wavelengths. For example, in one embodiment of the present invention, the wavelengths are time multiplexed by setting CS signal 212 to activate MUX 214, then setting SEL signal 210 to sequentially select LED 218, 222, 226, and 230, followed by a period deactivating MUX 214. FIG. 12 illustrates the signal output form a single light detector upon receiving the time multiplexed wavelengths of light as discussed above. The y-axis is a representative light intensity measurement. The x-axis represents time. It can be appreciated that if wavelength-dependent detectors are provided, which only detect a specified range of wavelengths, time multiplexing of the emitted light is not necessary.

For any given wavelength set, such as a pair of wavelengths, the measurement may be accurate only over a particular range. The embodiment of FIG. 11 utilizing control unit and light source of FIG. 12 advantageously produces a spectrum of wavelength measurements that can be combined to produce a more accurate measurement over a larger range of measurements. For example, for a set of two wavelength combinations with overlapping ranges of accurate measurements, $SpO_2$ can be determined by a single wavelength combination alone, if the measurement is in a non-intersecting area of the range, or can be calculated based on an average of the measurements for the two wavelength sets, if the measurement is in an intersecting area of the range.

In a further embodiment of the present invention, SPO$_2$ is determined using weighted averages of the received light intensities. The weighted average, X, of measurements $x_1$, $x_2$, $x_3$, ... $x_n$ may be represented mathematically as:

$$X = w_1 x_1 + w_2 x_2 + w_3 x_3 + \ldots w_n x_n$$

where $w_{1-n}$ are the weights corresponding to each measurement and:

$$w_1 + w_2 + w_3 + \ldots w_n = 1.$$

The weights can be assigned based on signal quality, noise, and/or assumptions about known trade-offs in particular wavelength combinations. Where the trade-offs and other effects are distinct, the proper choice of weights and wavelength combinations produce an increased accuracy in the overall measurement of SpO$_2$.

VIII. Multiple Optical Paths

Conventional pulse oximeters take measurements along a single optical measurement path. One problem encountered with the use of a single path is a relatively low usable signal time. For example, if a probe is temporarily dislodged due to motion on the part of the mother or baby, the pulse oximeter cannot return a measurement. The present invention minimizes the problem by taking measurements along multiple optical paths.

Figure 13:
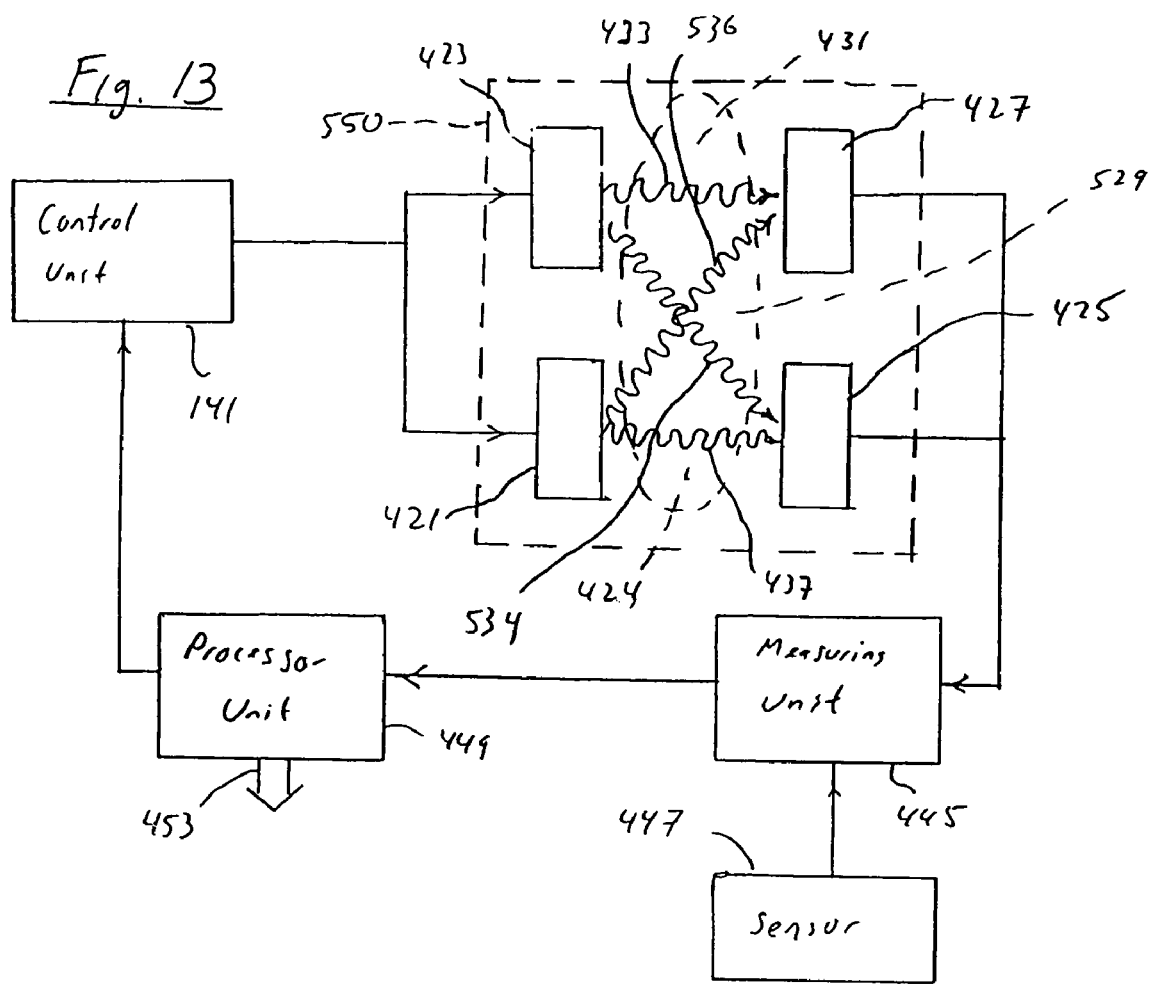
FIG. 13 is a block diagram of an optical measuring device according to the invention utilizing multiple optical paths.

FIG. 13 shows an embodiment according to the invention that provides multiple optical measurement paths 433 and 437 through tissues portions 429 and 431 positioned between or against light sources 421 and 423 and light detectors 425 and 427, respectively. A processor unit 449 is coupled to a control unit 441, which is coupled to light sources 421 and 423, to provide the overall system operation. In the illustrated embodiment, light source 421 emits a light that transmits through the tissue portion 429 to light detector 425 along optical measurement path 437, and light source 423 emits a light that transmits through tissue portion 431 to the light detector 427 along an optical measurement path 433. Light detectors 425 and 427 are coupled to a measuring unit 445 that measures the light intensity incident on light detectors 425 and 427. An additional sensor device 447 measures further parameters, such as a measurement, and is coupled to measuring unit 445 to provide correlation of the optical measurements with these other measurements. Processor unit 449 receives and processes the light intensity measurements from measuring unit 445 to produce a measurement 453.

An advantage of this embodiment is that problems along optical measurement path 433 do not necessarily impair measurements along optical measurement path 437, thereby improving the usable signal time. A fetal monitor, for example, could use two probe sites on opposite sides of the baby's head. Any motion that decreases pressure on one side (temporarily dislodging one probe) would be likely to increase pressure on the other side (holding the other probe in place). Processor unit 449 could then reject the poor signal and utilize the good signal to produce measurement 453. Of course, increasing the number of probe sites leads to even greater usable signal time, but this must be balanced against the time required to place the probe and potential discomfort to the mother and/or the baby.

A further advantage of this embodiment is that measurements from multiple optical measurement paths provide a spectrum of optical measurements that may be combined to increase accuracy as described in the previous paragraphs relating to the spectrum of wavelengths. For example, if both paths return good signals, the measurements from each path could be averaged to produce measurement 453. Alternatively, the measurement from each path could be weighted according to signal quality, noise, and/or other site specific characteristics and combined to produce a weighted average for measurement 453. In one embodiment, at least a pair of wavelengths of light are provide alone each optical measurement path, and the processing unit produces a measurement according to selectively weighted ratios of light measured from the two wavelengths of light along each of the plurality of optical measurement paths. In another embodiment, the processing unit produces a measurement according to selective weighting of one of the two wavelengths along each of the plurality of optical measurement paths.

Optical measurement along a single optical path has further disadvantages due to path dependent inaccuracies. For example, conventional pulse oximeters assume a constant physiological tissue optical absorbance and therefore the AC component is assumed to come from arterial sources only. These assumptions are inaccurate to varying extents depending on the optical path traversed. Another path dependent inaccuracy is caused by varying blood fraction, which is the ratio of blood to other tissue along the optical path. For example, calibration of a pulse oximeter is influenced by the amount of scattered light versus the amount of directly transmitted light which in turn depends on the blood fraction. The blood fraction, however, can be affected by physiological changes, anatomical stresses in the path, or by measurement site changes. The embodiment of FIG. 13 provides an advantage in that the inaccuracies due to the above assumption of constant physiological tissue optical absorbance and other path dependent properties in the computation of SpO$_2$ may be mitigated by counterbalancing the assumptions to effectively cancel each other out. Path dependent characteristics can be incorporated into the previously described weighted average to improve overall accuracy of the measurement.

A further embodiment of the present invention, which, for convenience, is also illustrated in FIG. 13, contemplates providing multiple measurement paths in one probe, rather than using separate probes discussed above. In this embodiment, light source 421 transmits light through tissue portion 437 to light detector 425 along an optical measurement path 437 and through tissue portion 529 to light detector 527 along an optical measurement path 536. Similarly, light source 523 transmits light through tissue portion 431 to light detector 427 along optical measurement path 433 and through tissue portion 529 to light detector 424 along an optical measurement path 534. Of course, it is possible to arrange light sources 421 and 423 and light detectors 425 and 427 so that light only travels along paths 433 and 437. In addition to a number of the previously discussed advantages relating to multiple optical measurement paths, the embodiment discussed above that uses a single probe to generate multiple light paths in that probe also has the advantage that a single probe site provides ease of application and minimal discomfort to the mother and the baby.

It can be appreciated from FIGS. 10-13 and the above discussion, that a multiple wavelength spectrum and the use of multiple optical measurement paths may be used independently or combined to provide an even more accurate measurement. For example, because different wavelengths have different penetration characteristics in different media, the accuracy of any wavelength pair depends on both the wavelength choice and the optical measurement path. Measurements taken from a spectrum of wavelengths along multiple optical paths may be combined to further mitigate inaccuracies due to wavelength or path dependent assumptions.

Figure 14:
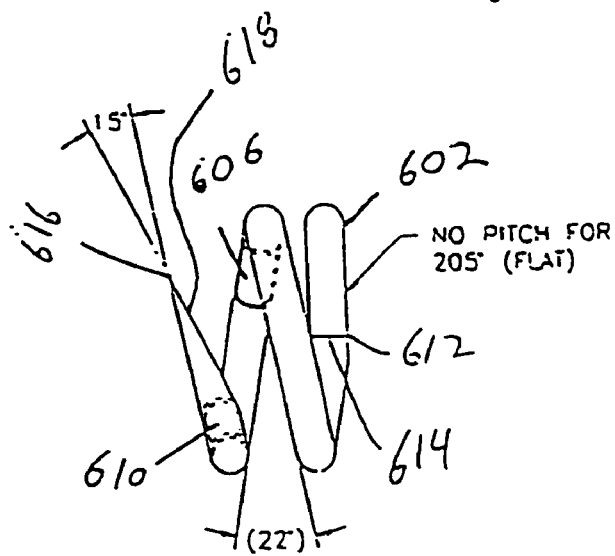
FIG. 14 is a side view of a spiral needle according to a further embodiment of the present invention.

FIG. 14 is a side view of an exemplary embodiment of the present invention that includes a hollow spiral needle 602 with an first opening 614 at its base 612 and a second opening 618 at its tip 616. Needle 602 also includes window openings 606 and 610. Preferably, the effective outer diameter of the spiral is 0.190 inches, the tube has an outside diameter of 0.028 inches and an inside diameter of 0.022 inches, the pitch between turns in the spiral is 0.063 inches and the height of the spiral is 0.124 inches. This embodiment provides an advantage in that it accommodates multiple optical paths within a single probe site.

A perspective view of a sensor 11' according to the principles of the present invention that utilizes needle 602 in FIG. 14 to provide multiple optical paths is shown in FIG. 15. Sensor 11' includes a hollow spiral needle 602 with opening 618 at its distal tip 616 and window openings 606 and 610 along its body. A first light source 621 is positioned in window opening 606 and transmits light along an optical measurement path 637 to a light detector (not shown) in window opening 610. A second light source 623 is centrally positioned on a top surface probe 650 to transmit light along optical measurement path 633 to a light detector (not shown) in tip opening 618. This embodiment provides good probe contact and improved tolerance of motion artifacts with relatively low invasiveness. These features, combined with the above described advantages pertaining to multiple optical measurement paths and multiple wavelength combinations, provide increased usable signal time and improved accuracy.

IX. Adapting Conventional Oximeters for Use with Fetal Pulse Oximeter System

Because the sensor in invasive fetal pulse oximetry is positioned under the skin during operation, the maximum current and voltages levels are typically limited to levels lower than non-invasive applications. Various diagnostic equipment are available for pulse oximetry applications, but are not suitable for an invasive application because of safety and other considerations. According to the invention, an adapter module may be used to provide an interface between diagnostic equipment and a sensor system according to the invention.

FIG. 16 is a block diagram of an oximetry system according to the invention. A measurement module 700 is connected to an adapter module 702 via a signal line 704. Adapter module 702 is connected to a connector 710 via a signal line 706. Measurement module 700 is also connected to connector 710 via a signal line 708. Connector 710 provides signals to and receives signals from a sensor 711 via a circuit connector 709. According to the principles of the present invention, signals provided from or received by measurement module 700, which are directly compatible with sensor 711, are provided to connector 710 over signal line 708. Signals which require modification or adaptation for use with sensor 711 are provided from measurement module 700 to adapter module 702 over signal line 704. The signals received from measurement module 700 are processed and provided to connector 710 over signal line 706.

As shown in FIG. 16, measurement module 700 is preferably supplied with a power source VCC1 and a ground reference GND1, while adapter module 702 is supplied with a power source VCC2 and a ground reference GND2. Power source VCC1 and ground reference GND1 are preferably electrically isolated from each other. Also, the interface between measurement module 700 and adapter module 702 is preferably made via opto couplers for further electrical isolation. For example, the Masimo MS-1 board and embodied SETÔ technology is made available by Masimo Corporation as a pulse oximetry measurement module. This technology may be useful for fetal oximetry, but the Masimo measurement module does not take into account the safety considerations discussed above with respect to invasive fetal oximetry and thus requires adaptation to be used with the sensor system according to the invention.

In an exemplary embodiment of the present invention, adapter module 702 adapts the Masimo measurement module for use with the sensor system of the present invention. To achieve this end, the current and/or voltage levels supplied by the Masimo measurement module need to be limited to safe levels for invasive fetal oximetry. Also, because all of the connections are made via closely spaced flexible circuit board conductors, it is preferable to have the LEDs driven differentially to avoid significant noise radiation from the LED circuit being picked up by the photodetector circuit and other nearby circuits. Using the differential LED drive also eliminates the LED circuit ground from having to be exposed at the patient, thereby avoiding inadvertent return paths for the LED current. To use the differential LED drive, the detector circuit power and ground are isolated from the LED circuit power and ground.

The Masimo measurement module provides the LED drive digital control signals to the adapter module, e.g., over signal line 704, via opto-couplers. The adapter module is supplied with power and ground from a circuit electrically isolated from the Masimo measurement module circuit which supplies power and ground to the photodetector circuits. The adapter module is configured with the LED differential drive, with the current and voltage levels limited to safe levels, and drives the LEDs in the sensor through the connector, e.g., via signal line 706. The LED circuit ground is not be available at the patient, thereby allowing no return path. The shielding for the circuit connector is obtained via the photodetector circuit ground. In the developed adapter module, the circuit connector, the connector, and the sensor correspond essentially to circuit connector 9, connector 10, and sensor 11.

Other considerations are made in order to adapt the Masimo measurement module for use with the invasive sensor of the present invention. For example, calibrating the sensor for the wavelengths used is done by introducing the calibration table into the MS-1 board software for the fetal range of measurement. A larger range of averaging times was introduced into the system, because the fetal application is interested in longer term trends. The algorithms for pulse rate detection were also modified for detection of fetal pulses.

X. Sensor Identification Using Sensor Interface

A further embodiment of the present invention provides the physiological monitoring device of the present invention with the ability to diagnose the status of the sensor assembly, which includes sensor 11 and circuit connector 9. For example, sensor conditions, such as sensor disconnected, sensor dislodged or off patient, and sensor defective (due to shorted or broken connectors) can be determined and provided to the user to diagnose and rectify such conditions. In fetal pulse oximetry, where the sensor is not easily visible or accessible, the importance of these diagnostic capabilities is especially desirable.

The present invention achieves this result by providing a diagnostic capability using a sensor identification resistor. Such a resistor provides a known resistance for the sensor circuit that can be detected by an external circuit, thereby deducing that the sensor is correctly connected. If the external circuit detects an incorrect value of the resistor, the sensor is not correctly attached or an unknown sensor is connected to the monitoring system. Similarly, if the system is calibrated to function with different sensors, each type of sensor can be provided with a different resistance value, so that the monitoring system can determine the type of sensor to which it is connected based on the detected resistance value and use the proper calculations, algorithms, tables etc., for that type of sensor, thereby providing correct information automatically without the user having to specify to the system the type of sensor being employed.

Conventional resistance based identification systems provide an identification resistor on the sensor portion of the circuit, which is past the patient interface where the sensor connects to the sensing system. Placing the resistance in the sensor itself, however, is likely to increase the cost of the sensor and the complexity of the manufacturing process, which is particularly undesirable if the sensor is to be a cost-effective, single-use sensor.

Figure 17:
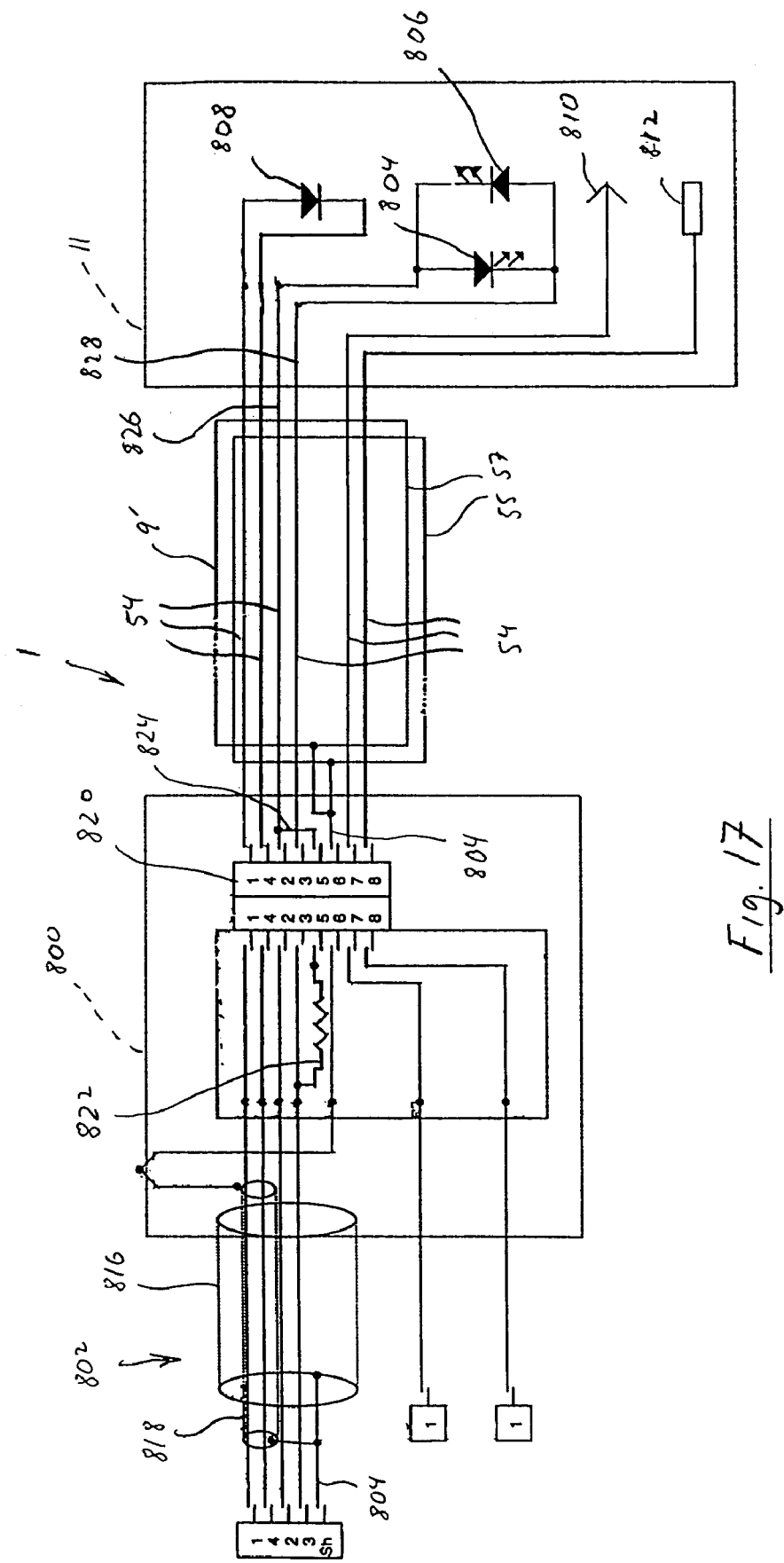
FIG. 17 is a schematic diagram of an interface that provides a sensor diagnostic and identification function.

The present invention avoids the shortcomings associated with the above described conventional techniques by providing the identification resistance at an interface (similar to interface 10 in FIG. 6) rather than on the sensor. FIG. 17 illustrates an exemplary embodiment of this feature of the present invention. As shown in FIG. 17, sensor system 1' includes sensor 11, a circuit connector 9', which is generally similar to circuit connector 9 discussed above, an interface 800 and connectors 802 that couple interface 800 to an external circuit (not shown). Sensor 11 includes light emitting diodes 804 and 806, light detecting diode 808, needle electrode 810, and reference electrode 61. Needle electrode 810 and reference electrodes 61 serve as EKG electrodes, for example.

Circuit connector 9' includes a plurality of conductors 54 that couple the elements of sensor 11 to an external circuit via interface 800. As discussed above, shield layers 55 and 57 are provided on either side of conductors 54 and are connected to ground via a ground line 814. In the illustrated embodiment, ground line 814 is also coupled to a conductive coating within the housing of interface 800 and to shield layers 816 and 818 in the cables electrically connecting the interface to an external circuit. The proximal ends of conductors 54 selectively couple to the conductors in interface 800 via a terminal 820, where pins on the left hand side are electrically coupled to like-numbered pins on the right hand side.

An identifying resistor 822 is provided on the left-hand side of terminal 820 across pins 3 and 5. Pins 3 and 5 on the left-hand side of terminal are disconnected from one another as long as circuit connector 9' is not coupled to terminal 820, thereby electrically isolating resistor 822. In which case, the external circuit recognizes the sensor assemble, which includes sensor 11 and circuit connector 9' as being disconnected. However, when circuit connector 9' is coupled to terminal 820, a bypass circuit 824 couples pins 2 and 5 on the right-hand side of terminal 820 thereby connecting resistor 822 cross conductors 826 and 828, which are the same conductors connected to the LED terminals. As a result, the external circuit sees resistor 822 between the LED terminals even though the resistor is not provided on sensor 11, as contemplated by the previous embodiment. In which case the external circuit recognizes the sensor assembly as being properly connected.

Bypass circuit 824 can be provided in a variety of ways and need not be provided at the location illustrated in FIG. 17. In one embodiment, for example, bypass circuit 824 is provided by physically connecting the terminals pads of the conductors that are coupled to pins 2 and 5 when the circuit connector is attached to terminal 820. However, the present invention contemplates that the conductors that couple to pins 2 and 5 can be connected to one another at any location in the sensor assembly.

Resistor 822 can have any suitable value that is recognizable by the external circuit. If the external circuit sees the proper resistance, it, therefore, knows what type of sensor assembly coupled to the interface. It is to be understood that other identification resistors can be provided in the interface and electrically coupled to the external circuit when a circuit connector is coupled to the interface so that different resistance values are seen by the external circuit depending on the type of sensor assembly being coupled to the interface. In this way, a variety of different types of sensor assemblies having different operating characteristics can be coupled to the interface and the external circuit can determine the type of sensor assembly coupled to the interface based on the value of the resistance that is caused to be seen by the external circuit as a result of the sensor assembly being coupled to the interface. Furthermore, the identification element need not be a resistor. Other passive or active electrical components can be used for the identification purposes so long as they are uniquely identifiable.

This embodiment illustrated in FIG. 17 is advantageous in that it avoids placing identification resistor 822 in the sensor assembly, which includes sensor 11 and circuit connector 9'. As a result, the sensor assembly can be manufactured as less cost and complexity than a sensor assembly that includes the identification resistor, thereby making it practical to dispose of the sensor assembly after each use, with the interface being used repeatedly.

While the embodiment has been discussed above with respect to adapting the Masimo measurement module for use with the present invasive fetal monitor, those skilled in the art will appreciate that an adapter module according to invention may be developed for use with other measurement modules. As described above, a sensor system according to various embodiments of the present invention include one or more of the following features:

1) a insertion rod/introducer assembly that protects the sensor before use;
2) an applicator on one end of the insertion rod that securely engages the sensor, but also provides over-torque protection and readily pulls off of the sensor after the sensor has been attached;
3) a handle on the other end of the insertion rod that facilitates turning the sensor together with its circuit connector;
4) a circuit connector that reduces motion artifact near the sensor, reduces noise effects, and provides a reliable ground reference;
5) a cost-effective circuit connector interface for attaching to diagnostic equipment;
6) a sensor that stays in the tissue better, more reliably, and reproducibly than conventional fetal monitoring devices;
7) an improved sensor cup for holding the needle in the cup during assembly;
8) a needle structure and manufacturing process which improves sharpness and strength of the needle, especially at the needle tip;
9) an improved window configuration in the needle;
10) an improved manufacturing process for the LED and photodetector circuits and for inserting these circuits into the needle;
11) a multi-path technique for transmitting light though different tissues to increase measurement accuracy;
12) a multi-wavelength technique for transmitting light though tissue at a variety of wavelengths to increase measurement accuracy; and 13) a sensor identification function in which an identification resistor is provided in the multi-use interface rather than on the single-use sensor.

As is well known in the art, oximetry probes include both reflectance type probes and transmissive type probes. Various aspects of the present invention can be used with either type. Furthermore, while the invention has been discussed above as providing a light source (an LED in the above embodiments) within the needle or on the cup holding the needle, it should be understood that the light source need not be located in the needle. For example, the light source can be an LED or laser located external to the sensing system with light being carried from the light source to the needle via optical fiber where it is transmitted into the patient. Similarly, the light detector need not be in the needle so long as a light collector is provided at the light receiving locations in the needle or cup and is transmitted via an optical fiber, for example, to the light detecting element.

Given the disclosure of the present invention, one versed in the art would appreciate that there are other embodiments and modifications of the embodiment described above that are within the scope and spirit of the present invention. Accordingly, all modifications attainable by one versed in the art within the scope and spirit of the present invention are included as further embodiments of the present invention. The scope of the present invention is to be defined as set forth in the appended claims.

What is claimed is:

1. A physiological condition measuring device comprising:
   an insertion rod;
   a sensor selectively attached to a distal end of said insertion rod;
   a circuit connector having a distal end coupled to said sensor and a proximal end that selectively couples said sensor to an external circuit;
   an introducer tube selectively positioned relative to said insertion rod so as to house at least a portion of said insertion rod therein with said circuit connector extending along at least a portion of a length of said insertion rod between said insertion rod and said introducer tube, said introducer tube being moveable in an axial direction relative to said insertion rod;
   a mechanism that selectively couples said insertion rod and said introducer tube to maintain said introducer tube in a first position relative to said insertion rod wherein said sensor is located entirely within said introducer tube and that permits said introducer tube to be moved to a second position relative to said insertion rod wherein at least a portion of said sensor is located outside said introducer tube;
   wherein said mechanism is a deflectable tab disposed on said insertion rod, said tab being deflectable from a non-deflected position to a deflected position, in said deflected position, said tab provides a configuration that permits a first portion of said tab to insert between a portion of said introducer tube and said insertion rod, with said tab being biased into an engaged relation with said introducer tube to maintain said introducer tube in said first position, and wherein removing said tab from within said introducer tube causes said tab to move to its non-deflected position out of a path of movement of said introducer tube relative to said insertion rod to permit said introducer tube to be moved to said second position; and
   further comprising a first tab provided on a side of said insertion rod opposite a side on which said deflectable tab is located, said first tab being sized and configured to provide a force on said introducer tube opposite a force provided thereon by said deflectable tab responsive to said deflectable tab being biased into said engaged relation with said introducer tube.

2. A physiological condition measuring device comprising:
   an insertion rod;
   a sensor selectively attached to a distal end of said insertion rod, said sensor and an associated portion of said insertion rod being sized and configured such that said sensor rotates relative to said insertion rod if a torque applied on said sensor by said insertion rod exceeds a first predetermined amount and said sensor disconnects from said distal end of said insertion rod if a pull-off force exerted on said sensor by said insertion rod exceeds a second predetermined amount, wherein said first predetermined amount of torque necessary to cause rotation is independent of said second predetermined amount of force necessary to cause said sensor to disconnect from said insertion rod;
   a circuit connector having a distal end coupled to said sensor and a proximal end that selectively couples said sensor to an external circuit;
   an introducer tube selectively positioned relative to said insertion rod so as to house at least a portion of said insertion rod therein with said circuit connector extending along at least a portion of a length of said insertion rod between said insertion rod and said introducer tube, said introducer tube being moveable in an axial direction relative to said insertion rod;
   an applicator provide at said distal end of said insertion rod to selectively attach said sensor to said insertion rod, wherein said applicator includes a plurality of walls defining an opening, each wall being attached at its base to a remainder of said applicator and being separated from adjacent walls by a slot so that each wall is adapted to flex in a direction generally perpendicular to its base to permit rotation of said sensor within said opening if said torque applied on said sensor by said insertion rod via said applicator exceeds said first predetermined amount; and
   wherein said sensor includes a cup and a needle mounted in said cup, said cup having a base portion adapted to fit within said opening defined by said plurality of walls, wherein said base portion includes at least one protrusion on a surface thereof, and wherein an interior surface of at least one of said walls includes a groove, said protrusion and said groove being sized and configured such that said grooves selectively receives said protrusion responsive to said base portion of said cup being disposed in said opening of said applicator.

3. A physiological condition measuring device according to claim 2, wherein said cup has a slit defined at a side there, said slit providing a passageway from an interior cavity of said cup to an external portion of said cup, said passageway being defined by four walls and being sized to receive said distal end of said circuit connector.

* * * * *